Figure 2:
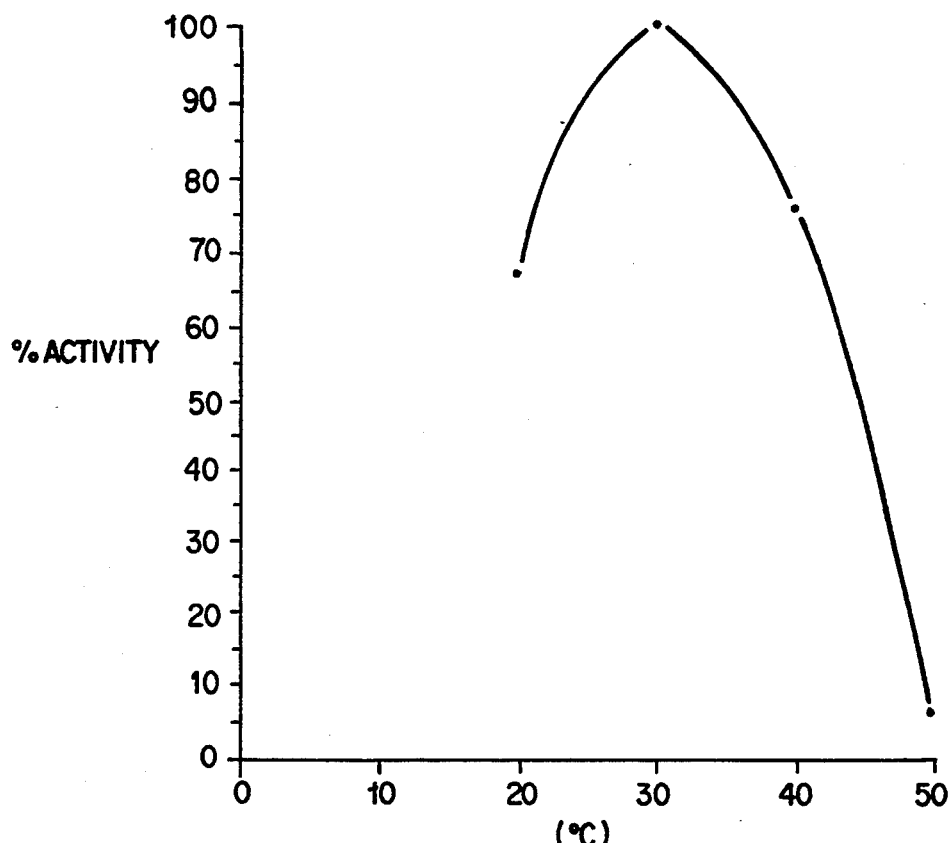

United States Patent [19]

Moeller et al.

[11] Patent Number: 5,427,936
[45] Date of Patent: Jun. 27, 1995

[54] ALKALINE BACILLUS LIPASES, CODING DNA SEQUENCES THEREFOR AND BACILLI, WHICH PRODUCE THESE LIPASES

[75] Inventors: Bernhard Moeller, Hanover; Roman Vetter, Burgdorf; Detlef Wilke, Wennigsen; Birgit Foullois, Hanover, all of Germany

[73] Assignee: Kali-Chemie Aktiengesellschaft, Hanover, Germany

[21] Appl. No.: 930,678

[22] PCT Filed: Apr. 8, 1991

[86] PCT No.: PCT/EP91/00664

§ 371 Date: Oct. 13, 1992

§ 102(e) Date: Oct. 13, 1992

[87] PCT Pub. No.: WO91/16422

PCT Pub. Date: Oct. 31, 1991

[30] Foreign Application Priority Data

Apr. 14, 1990 [DE] Germany .................. 40 12 070.8

[51] Int. Cl.⁶ .................. C12N 9/20; C12N 15/55; C12N 1/20
[52] U.S. Cl. .................. 435/198; 435/252.1; 536/23.2
[58] Field of Search .................. 435/198, 252.1; 536/23.2

[56] References Cited

U.S. PATENT DOCUMENTS 5,093,256  7/1992  Shen et al. .................. 435/198

FOREIGN PATENT DOCUMENTS 334462  9/1989  European Pat. Off.

OTHER PUBLICATIONS

Chemical Abstract 188319d, vol. 94, No. 23, p. 301, (1981).
Chemical Abstract 130743g, vol. 113, No. 15, p. 521, (1990).

*Primary Examiner*—Keith C. Furman
*Attorney, Agent, or Firm*—Evenson, McKeown, Edwards & Lenahan

[57] ABSTRACT

The invention relates to alkaline *bacillus lipases*, DNA sequences, which code for these *lipases*, a method for isolating and producing these *lipases*, as well as to *bacillus* strains, which have the capability to form these *lipases*. The alkaline *lipases* are suitable for use in compositions for cleaning, washing and bleaching purposes.

7 Claims, 15 Drawing Sheets

```
CCAAGGTGCT TTTTGATTAT TTATATTTTT GTAAAATCAT CTCATAAACA         50
TTACCTTGTT CACTTTTCTG ACATATTTTT CTTGTATAAA ATAGAGTCGT        100

ATAAGATGAA TAAGGGGGAA TGAAA GTG ATT TTT GTT AAG AAA           143
                            Met Ile Phe Val Lys Lys
                                -30

AGG AGT TTG CAA ATT CTC ATT GCG CTT GCA TTG GTG ATT           182
Arg Ser Leu Gln Ile Leu Ile Ala Leu Ala Leu Val Ile
    -25             -20                 -15

GGT TCA ATG GCG TTT ATC CAG CCG AAA GAG GCG AAG GCG           221
Gly Ser Met Ala Phe Ile Gln Pro Lys Glu Ala Lys Ala
        -10              -5                      -1

GCT GAG CAT AAT CCG GTT GTG ATG GTG CAC GGC ATT GGC           260
Ala Glu His Asn Pro Val Val Met Val His Gly Ile Gly
 1                5                  10

GGT GCC TCT TAT AAC TTT TTT TCT ATT AAA AGT TAT TTG           299
Gly Ala Ser Tyr Asn Phe Phe Ser Ile Lys Ser Tyr Leu
     15              20                  25
```

FIG. 1A

```
GCC ACA CAA GGC TGG GAT CGA AAC CAA TTA TAT GCT ATT
Ala Thr Gln Gly Trp Asp Arg Asn Gln Leu Tyr Ala Ile    338
         30                      35

GAT TTC ATA GAC AAA ACA GGA AAT AAC CGC AAC AAT GGT
Asp Phe Ile Asp Lys Thr Gly Asn Asn Arg Asn Asn Gly    377
         40              45                  50

CCG CGT CTA TCG AGA TTC GTC AAA GAT GTG TTA GAC AAA
Pro Arg Leu Ser Arg Phe Val Lys Asp Val Leu Asp Lys    416
         55                  60                  65

ACG GGT GCC AAA AAA CTA AAA GTA GAT ATT GTG GCT CAT AGT ATG
Thr Gly Ala Lys Lys Leu Lys Val Asp Ile Val Ala His Ser Met    455
         70                                  75

GGA GCG AAC ACG CTA TAC TAT ATC AAG AAT CTA GAT
Gly Ala Asn Thr Leu Tyr Tyr Ile Lys Asn Leu Asp    494
                     85                  90

GGC GAT AAA ATT GAG AAC GTT GTC ACA ATT GGT GGA
Gly Asp Lys Ile Glu Asn Val Val Thr Ile Gly Gly    533
         95                         100
```

FIG. 1B

```
GCA AAC GGA CTC GTT TCA AGC AGA GCA TTA CCA GGC ACA          572
Ala Asn Gly Leu Val Ser Ser Arg Ala Leu Pro Gly Thr
            110                     115

GAT CCA AAT CAA AAA ATT CTT TAC ACA TCC GTC TAT AGC          611
Asp Pro Asn Gln Lys Ile Leu Tyr Thr Ser Val Tyr Ser
        120                     125                 130

TCA GCA GAT CTT ATT GTC GTC AAC AGC CTC TCT CGT TTA          650
Ser Ala Asp Leu Ile Val Val Asn Ser Leu Ser Arg Leu
                135                     140

ATT GGC GCA AGA AAC ATC CTG ATC CAT GGC GTT GGT CAT          689
Ile Gly Ala Arg Asn Ile Leu Ile His Gly Val Gly His
145                     150                     155

ATC GGT CTA TTA ACC TCA AGC CAA GTG AAA GGG TAT ATT          728
Ile Gly Leu Leu Thr Ser Ser Gln Val Lys Gly Tyr Ile
        160                     165

AAA GAA GGA CTG AAC GGC GGA CAA AAT ACG AAT TAAAAAAACGA      744
Lys Glu Gly Leu Asn Gly Gly Gln Asn Thr Asn
170                     175                 180

AAAAAGACAG CGGCATATG                                         793
```

FIG.1C

ALKALINE BACILLUS LIPASES, CODING DNA SEQUENCES THEREFOR AND BACILLI, WHICH PRODUCE THESE LIPASES

The present invention relates to alkaline *bacillus lipases* and to DNA sequences, which code for these *lipases*, to the use and to a method for producing these *lipases*, as well as to the *bacillus* strains, which are capable of forming these *lipases*.

Enzymatic compositions for washing, cleaning and bleaching applications are well known in the art. Admittedly, various types of enzymes have already been proposed for these applications. However, the main interest has been directed essentially to the proteases and amylases. The *lipases*, previously proposed in the art for washing, cleaning and bleaching compositions, were obtained by culturing microorganisms such as *pseudomonas, rhizopus, chromobacter* and *humicola species* (including *thermomyces species*).

Although such *lipases* have been considered as possible enzymes for the applications cited, *lipases* have hardly gained any acceptance previously in washing, cleaning and bleaching compositions, since various constituents of these compositions have a negative effect on the activity of the *lipases*. For example, it is well known that synthetic anionic surfactants, in particular, have a negative effect on lipase activity. Admittedly, of the plurality of enzymes known in the art, which belong to the class of *lipases*, each individual enzyme also has special, advantageous properties. Nevertheless, the possibilities of employing these enzymes are limited because of their disadvantageous properties.

Moreover, the *lipases*, since they themselves also are proteins, are subject to the proteolytic degradation by detergent proteases, if they are used in combination with these proteases as detergent components of washing, cleaning and bleaching compositions. As a result, the danger exists that, when protease and lipase are used together in this composition, the lipolytic activity cannot be utilized at all or utilized only partly because of the lipolytic activity losses.

On the other hand, fats and oils are removed only poorly and incompletely from the fabrics and/or objects that are to be cleaned, particularly at low washing and cleaning temperatures, such as temperatures up to 40° C., if the washing and cleaning process is not supported by lipolytically effective enzymes.

It is therefore an object of the invention to make available such *lipases*, which are useful as additives for detergent, cleaning agent and bleaching agent compositions and have a high activity at temperatures up to 40° C. and a versatile applicability in the presence of proteases and over a wide pH range and particularly in a neutral to alkaline pH range.

Surprisingly, it has now been discovered that *lipases*, which are secreted by *bacillus species*, have the desired properties with a pH optimum in the alkaline pH range and a temperature optimum between about 30° and 40° C. In appropriate refinements of the invention, it is a question particularly of alkaline *bacillus lipases*, which can be obtained by culturing *Bacillus pumilus*.

In preferred embodiments of the invention, particularly those alkaline *bacillus lipases* of the aforementioned species are present, which have an amino acid sequence, which is at least 70%, preferably at least 80% and particularly at least 90% homologous with the amino acid sequence given in FIG. 1 (SEQ ID NO:2).

Homology is understood here to be the degree of relationship of the amino acid sequence in question of a *bacillus lipase* to the amino acid sequences of the *lipases* from the natural *bacillus* isolates DSM 5776, DSM 5777 or DSM 5778 and, in particular to the amino acid sequence (SEQ ID NO:2) of the lipase from the natural *bacillus* isolate DSM 5776, as given in FIG. 1 (SEQ ID NOS:1 and 2). To determine the homology, in each case the sections of amino acid sequence of the *lipases* from the natural *bacillus* isolates, particularly the sections of the amino acid sequence of FIG. 1 (SEQ ID NO:2) and an amino acid sequence of a *bacillus lipase*, which is to be compared therewith, are superimposed, so that there is maximum agreement between the two amino acid sequences, differences caused by the deletion or insertion of individual amino acids being taken into consideration and compensated for by appropriately shifting the sequence sections. The number of amino acids, which now coincide with one another in the sequences ("homologous positions"), based on the total number of amino acids contained in the sequence of one of the *lipases* from the cited natural *bacillus* isolates, thus gives the homology as a percentage. Deviations in the sequences can be caused by variation, insertion as well as deletion of amino acids.

In a highly preferred embodiment of the invention, the inventive *lipases* are, in particular, alkaline *bacillus lipases*, which can be obtained by culturing Bacillus pumilus of the DSM 5776, DSM 5777 or DSM 5778 species and can be isolated, for example, as described further below.

The new alkaline *bacillus lipases*, proposed by the invention, particularly have the following additional properties:

(1) Effect: breakdown of triglycerides and fatty esters;

(2) pH optimum: at a pH of about 9 to 10;

(3) pH stability: at a pH from 6.5 to 11, the enzymes prove to be completely stable; after incubation at a pH of 11 and a temperature of 4° C. for 21 hours, the residual activity of the enzymes is at least 90%;

(4) Temperature optimum: about 30° to 40° C.;

(5) Temperature stability: the activity of the enzymes is not affected significantly by incubation for 30 minutes at temperatures up to 40°; after incubating for 30 minutes at 40° C., the residual activity of the enzymes is at least 90%.

The inventive *bacillus lipases* are suitable advantageously as additives for detergents and cleaning agent compositions, etc., which have neutral to alkaline pH values and are to be used at low temperatures, particularly at temperatures up to 40° C. The invention therefore also relates to the use of the inventive, alkaline *bacillus lipases* in detergent, cleaning agent, bleaching agent or dish-washing detergent compositions. They can also be advantageously be used in the presence of other conventional enzymes, particularly also in the presence of proteases. A highly preferred use of the inventive alkaline *bacillus lipases* relates to their use in detergent, cleaning agent, bleaching agent or dish-washing detergent compositions that are to be used at low temperatures, preferably at temperatures of about 30° to 40° C. For these applications, the invention makes available a group of new alkaline *lipases* from *bacillus species* with improved properties, the use of which also leads to advantageous detergent, cleaning agent, dish-washing-detergent and bleaching agent compositions. The invention therefore furthermore comprises these advantageous compositions for washing, cleaning, bleaching or washing dishes, which contain the inventive, alkaline *bacillus lipases*. Embodiments of these compositions contain the inventive, alkaline *bacillus lipases* in the presence of protease. Preferred embodiments of the above compositions are distinguished by containing the alkaline *bacillus lipases* in a formulation for low application temperatures, preferably for application temperatures of about 30° to 40° C.

The inventive *lipases* can be used in detergent and cleaning agent formulations, such as powdered detergent formulations, individually or also, if so desired, in combination with one another and also in combination with detergent and cleaning agent proteases of the state of the art or other enzymes customarily employed in such compositions, such as *amylases, lipases, pectinases, nucleases, oxidoreductases*, etc. The inventive *lipases* are used in detergent and cleaning agent formulations in amounts customary for detergent enzymes (for example, amounts of about 0.1 percent by weight are already suitable), in particular, in an amount of up to 3 percent by weight (based on the dry matter of the total composition) and preferably in an amount of 0.2 to 1.5 percent by weight.

Aside from the already mentioned detergent enzymes, the inventive detergents and cleaning agents can contain detergent components customary in the art, such as surfactants, bleaching agents or builders, as well as further, additional auxiliaries for the formulation of detergents in conventional amounts. The auxiliaries include, for example, boosters, enzyme stabilizers, antiredeposition agents and/or compatibilizing agents, complexing and chelating agents, foam controllers and additives such as optical brighteners, opacifiers, corrosion inhibitors, antistats, dyes, bactericides, bleaching agent activators, peracid bleach precursors.

In a typical composition, the inventive detergent formulations contain, based on the dry substance, for example a) at least 5 percent by weight, for example 10 to 50 percent by weight of a surfactant or surfactant mixture, c) up to 40 percent by weight of a builder or a builder mixture, c) up to 40 percent by weight of a bleaching agent or a bleaching agent mixture, preferably a perborate, such as sodium perborate tetrahydrate or sodium perborate monohydrate, d) 0.1 to 3 percent by weight and preferably 0.2 to 1.5 percent by weight of at least one inventive lipase and, optionally, 0.1 to 3 percent by weight of a protease, e) other components, such as auxiliaries, etc. up to 100 percent by weight.

Such detergent formulations can be formulated in the usual manner. The inventive *lipases* can be mixed for this purpose in a known manner in the form of, for example, granulates, prills or pellets with the other components of the detergent formulation.

The inventive *bacillus lipases* are, moreover, very suitable for use in conventional liquid cleaning formulations, such as dishwashing agents or in liquid detergent formulations. The inventive *lipases* can also be introduced in the form of liquid enzyme formulations into these formulations.

The inventive alkaline *bacillus lipases* can be obtained, to begin with, by culturing in the usual manner a bacterium, which belongs to the genus *bacillus* and is capable of forming the alkaline lipase. After that, the cells are separated, for example by filtration or centrifugation, the enzyme is concentrated by membrane filtration or precipitation, purified, optionally also isolated and made available for the desired use.

On the one hand, for example, the natural isolates of *bacillus* strains themselves, which produce the inventive *lipases*, for example, prove to be suitable for producing and obtaining the inventive *lipases*. Such *bacilli* can be isolated from nature by first of all storing, for example, material containing animal or vegetable fat for some time under conditions suitable for *bacillus species* that excrete lipase, then optionally pasteurizing this material and subsequently inoculating a medium suitable for the growth of lipase-secreting *bacillus species* with the sample so obtained. After an adequate incubation time, the vegetative cells are killed by a heat treatment of the culture and the culture, so treated and optionally after being adjusted by a suitable dilution, is streaked out on, for example, lipase-screening plates and the plates are subsequently incubated. Alter a sufficiently long incubation period, the lipase screening plates are then examined by a known procedure for lipase-forming colonies and these colonies are isolated in a known manner. In this way, suitable natural *bacillus* isolates, which form an alkaline *bacillus lipase*, can be obtained. Examples are species of *Bacillus pumilus*, particularly the natural *bacillus* isolates, which also represent an object of the invention and which were deposited with the German Collection of Microorganisms, Federal Republic of Germany, on 2-7-1990 under the numbers DSM 5776, DSM 5777 and DSM 5778.

On the other hand, other *bacillus* strains, in which the necessary genetic information concerning the inventive *lipases* and their expression has previously been inserted by transformation, can also be used in an advantageous manner, particularly for reasons of simplifying and optimizing the production and increasing the yield, for producing and extracting the inventive *bacillus lipases*.

The invention therefore also comprises a method for the production of the inventive alkaline *lipases* with transformed microorganisms, preferably with transformed bacilli, which contain a vector with such a DNA sequence, which codes for an amino acid sequence of one of the inventive, alkaline *bacillus lipases* described further above.

The microorganism, transformed pursuant to the invention, is cultured and the alkaline *bacillus lipase* is isolated from the culture medium as described above. Preferred, transformed microorganisms for the production and extraction of the inventive *bacillus lipases* are *bacillus species* such as *Bacillus subtilis, Bacillus alcalophilus, Bacillus licheniformis* or *Bacillus amyloliquefaciens*. The microorganisms, suitably transformed pursuant to the invention for the expression of *bacillus lipases*, are characterized in that they are transformed with a vector, which contains the genetic information for one of the inventive, alkaline *bacillus lipases*. The genetic information for these inventive *bacillus lipases* is given in each case by a DNA sequence, which codes for an alkaline *bacillus lipase* with an amino acid sequence, which has at least a 70%, preferably at least an 80% and particularly at least a 90% homology with the amino acid sequence given in FIG. 1 (SEQ ID NO:2). These new DNA sequences, the vectors, preferably expression vectors, which are suitable for the transformation of microorganisms and contain these new DNA sequences, as well as the microorganisms transformed with these vectors, preferably bacilli so transformed as, particularly, the species given above, are also an object of the invention.

The following procedure can be employed to produce the transformed microorganisms, used in the above method:
  a) to begin with, the DNA sequence coding for the *lipase* (that is, the structure gene of the lipase) is isolated from a suitable *bacillus* strain, which produces an alkaline lipase with an amino acid sequence with at least 70%, preferably at least 80% and particularly at least 90% homology with the amino acid sequence given in FIG. 1 (SEQ ID NO:2,
  b) optionally, the nucleotide sequence, of this DNA sequence is determined in order to identify the lipase further,
  c) subsequently, an expression vector is produced with the help of the isolated DNA sequence and
  d) the expression vector obtained is transformed in a suitable microorganisms, which can finally be used for the production of the alkaline lipase.

The process steps for isolating and extracting the inventive alkaline *lipases* according to the method above, as well as the hereby obtained intermediates in the form of DNA sequences or DNA inserts with the lipase gene, vectors, particularly expression vectors, and transformed microorganisms, which partly also represent an object of the invention, are described in detail in the following.

The structure genes, which code for the amino acid sequence of the alkaline *bacillus lipases*, can be obtained by well-known, general methods. For this purpose, the chromosomal DNA is isolated by well-known methods from, for example a *bacillus* (the donor *bacillus*), which produces an alkaline lipase, particularly from a *bacillus* of the DSM 5776, DSM 5777 or DSM 5778 group, and partially hydrolyzed with suitable restriction endonucleases. Restriction endonucleases are enzymes, which split double-stranded DNA substrate specifically into fragments because they split phosphodiester bonds between individual nucleotide components of the DNA. All restriction endonucleases are capable of recognizing certain base sequences of the DNA, which mark sites of action (intersections) specific for the activity of the restriction nucleases in question. When double-stranded DNA is cut (restriction), as it is here, specific, so-called "overhanging ends" are produced, which can be combined (ligated) once again with one another or with appropriate (complementary) overhanging ends of otherwise obtained DNA fragments (recombination). When cutting with other restriction endonucleases, DNA double strands with smooth ends are produced. These DNA double strands with smooth ends can be recombined with any DNA double strands, which also have smooth ends.

The restriction fragments of the donor DNA obtained can be separated according to size by gel electrophoresis or centrifuging through a sucrose density gradient column and the fragments of the desired size can then be recombined with a suitable, double-stranded vector DNA. Vectors are DNA molecules, which are suitable as transport molecules (vehicles) for the infiltration (transformation) of foreign DNA into host cells, can be reproduced there autonomously and possibly also have so-called markers. Markers are DNA fragments, which code for certain observed properties (such as resistance to antibiotics) and can be used for the subsequent selection of the transformed microorganisms (transformants). The so-called plasmids are frequently used as vectors. They are extrachromosomal, ring-shaped, double-stranded bacterial DNA, which can be inserted by suitable methods in other microorganisms and reproduced there. A plasmid, which is used here and has the name of pUB 110, can be isolated, as described in greater detail in the examples, from the commercially available *Bacillus subtilts* BD366.

The above obtained DNA, recombined in vitro, can now be introduced into suitable host cells, such as the commercially obtainable strain of Bacillus subtilts PSL 1, which is used here. Transformants can be selected with the help of known markers on the vector DNA (for example, neomycin resistance). Among these antibioticresistant transformants, it is possible to search for lipase-secreting clones, that is, genetically identical transformants. Finally, the plasmid DNA, introduced into this transformant, is isolated from a clone with lipase activity and checked by a renewed transformation of a bacterium, particularly of a *bacillus species*, to see whether the lipase activity is plasmid-linked and coupled with the marker property.

Aside from the vector DNA (here, in particular, from the plasmid pUB110) with known restriction sites, the plasmid so isolated contains the desired structure gene for the sought-after alkaline *bacillus lipase* and, optionally, for further DNA sequences from the donor sequences, which are, however, not required here. Examples of these vectors with fragments (inserts) containing the lipase gene, are the plasmids with the names pL2-22-11, pL4-23-14 and pL11-8-20. The DNA sequences coding for the respective *bacillus lipases* and the associated amino acid sequences in these plasmids can be sequenced with the help of methods known in the art. The DNA sequence or the associated amino acid sequence given in FIG. 1 (SEQ ID NOS: 1 and 2) is obtained, for example in this way.

The ability of these plasmids, for examples the plasmids pL2-22-11, pL4-23-14 and pL11-8-20 to express the alkaline *bacillus lipase* can be checked by transforming a bacterium, particularly a *bacillus species*, with one of these plasmids and culturing the transformant so obtained and checking for lipase activity. The transformants obtained can, moreover, also be cultured for the production and extraction of the inventive alkaline *bacillus lipases*, the inventive alkaline *lipases*, described further above, then being obtained.

The inventive *bacillus lipases* are distinguished by advantageous properties. They have a favorable pH stability over a wide pH range from pH 5 to pH 11 and are completely stable at a pH ranging from 6.5 to 11. The optimum pH of the inventive *bacillus lipases* falls within the range of pH 9 to pH 10, which is favorable for use in detergent and cleaning agent compositions. Moreover, the inventive *lipases* have a temperature optimum between 30° and 40° C. Furthermore, they also exhibit outstanding stability in suds, as well as in the presence of detergent proteases. Because of their advantageous activity at temperatures up to 40° C., the inventive *bacillus lipases* are suitable particularly for use in cleaning agent and detergent compositions, which are to be used at low temperatures, particularly at temperatures up to 40° C. Such detergent and cleaning agent compositions, which contain an inventive lipase, exhibit excellent laundering effectiveness with respect to oils and/or fats, which are to be removed.

Explanations of the Figures:

FIG. 1: DNA sequence protocol (SEQ ID NO:1) and associated amino acid sequence (SEQ ID NO:2) of the lipase from *Bacillus pumilus* DSM 5776

Figure 3:
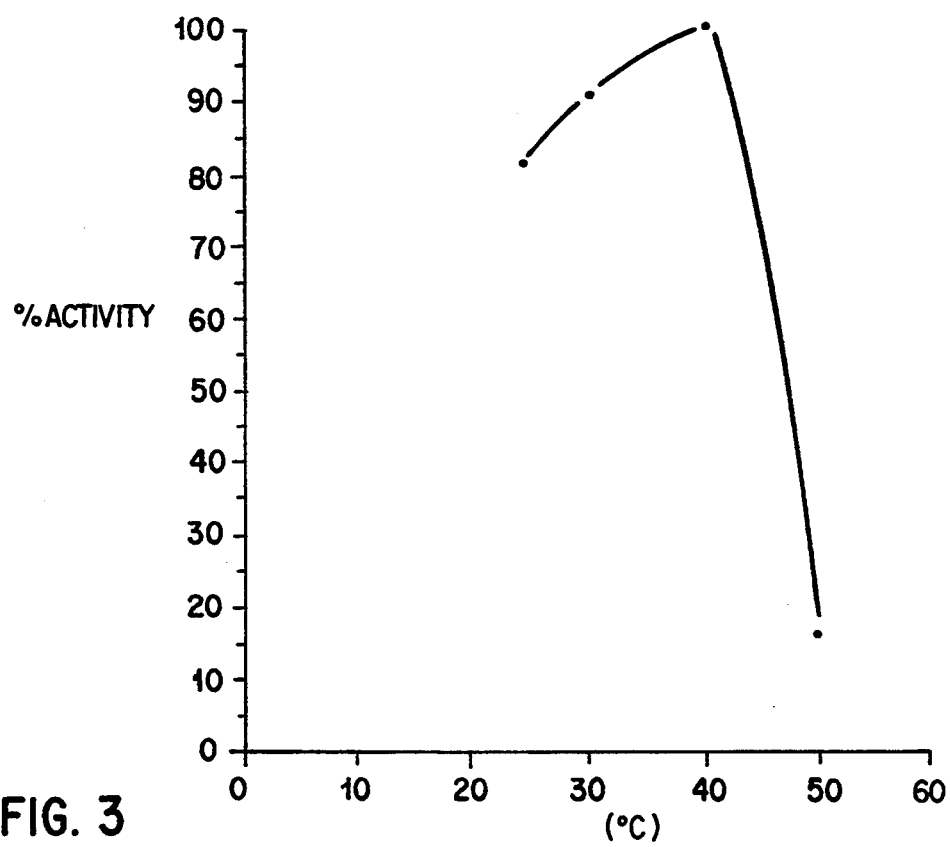
Figure 4:
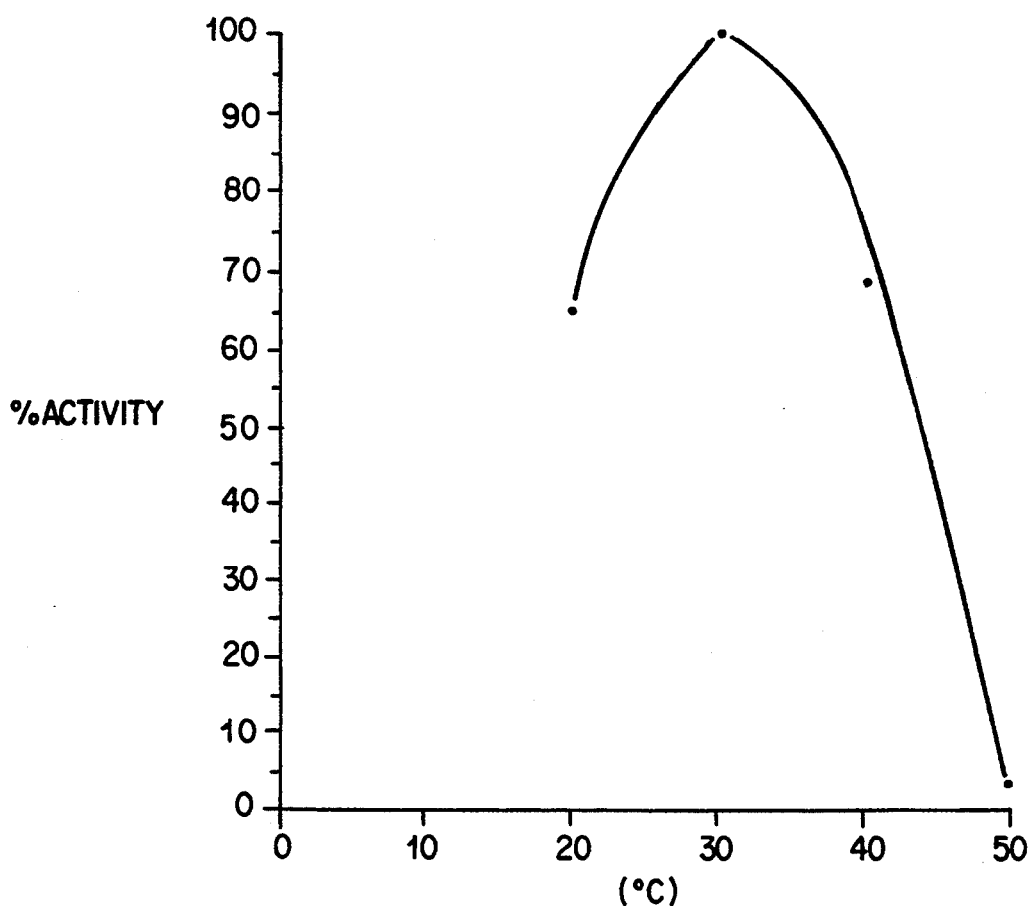

FIGS. 2 to 4: Curves for the temperature optima of the *lipases* from *Bacillus pumilus* DSM 5776 (FIG. 2), from *Bacillus pumilus* DSM 5777 (FIG. 3) and from *Bacillus pumilus* DSM 5778 (FIG. 4).

Figure 5:
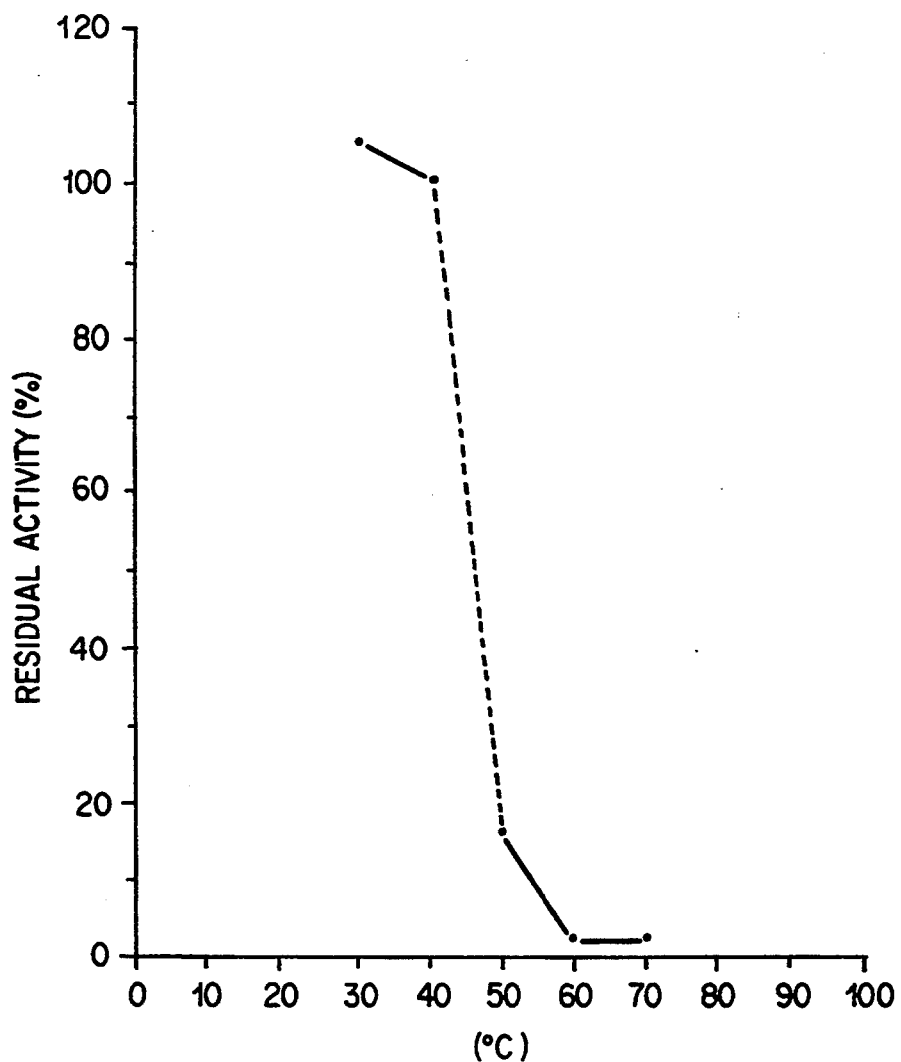
Figure 6:
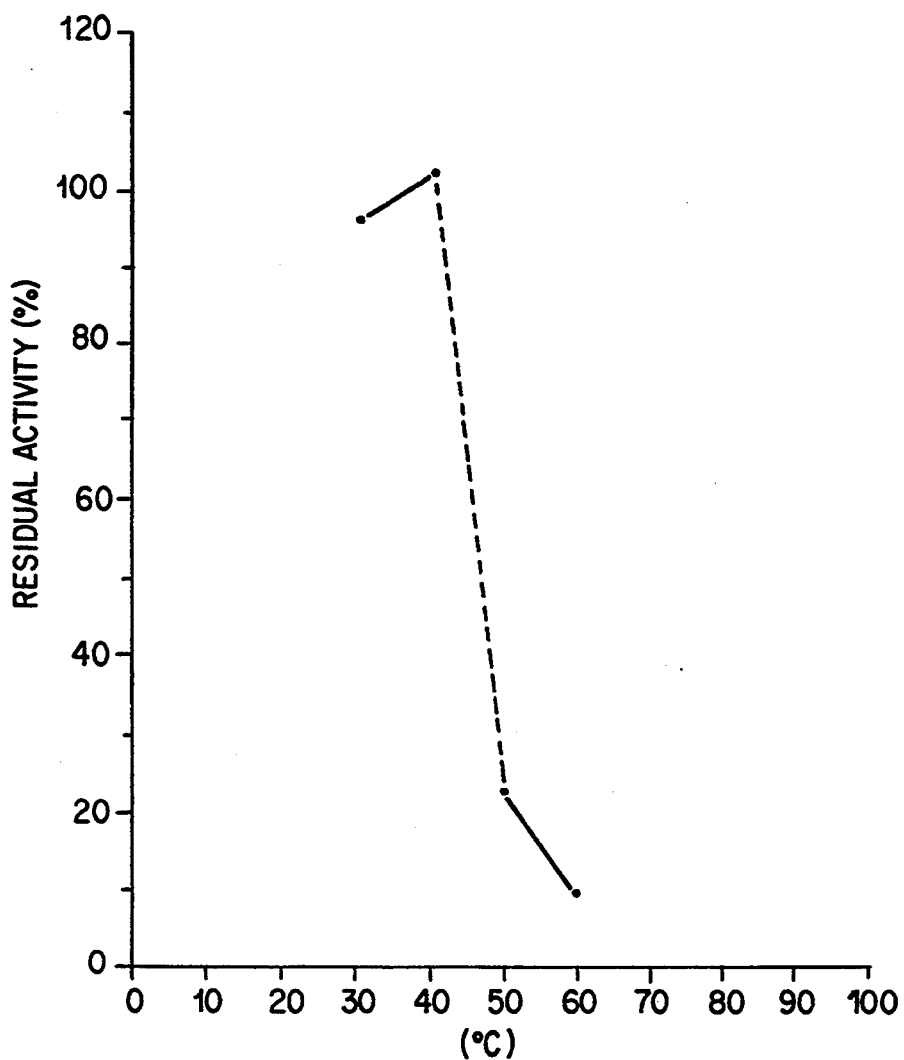
Figure 7:
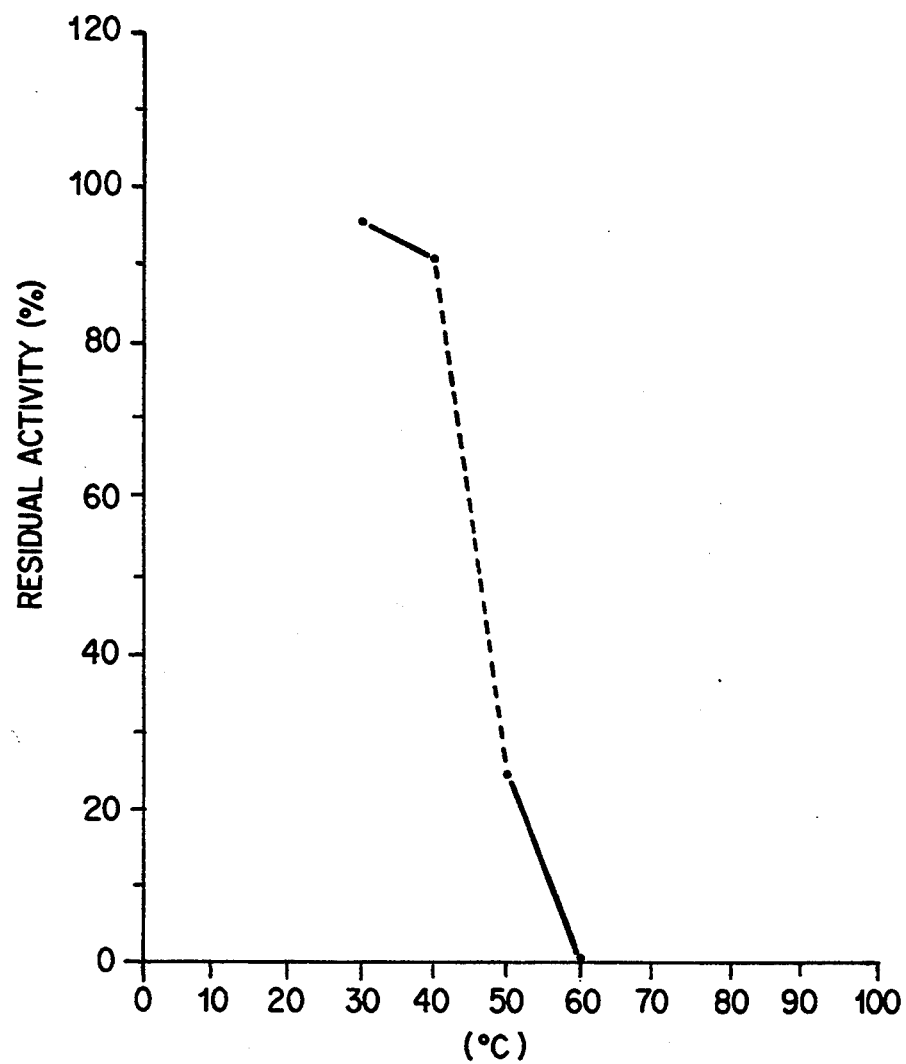

FIGS. 5 to 7: Curves for the temperature stability of the *lipases* from *Bacillus pumilus* DSM 5776 (FIG. 5), from *Bacillus pumilus* DSM 5777 (FIG. 6) and from *Bacillus pumilus* DSM 5778 (FIG. 7).

Figure 8:
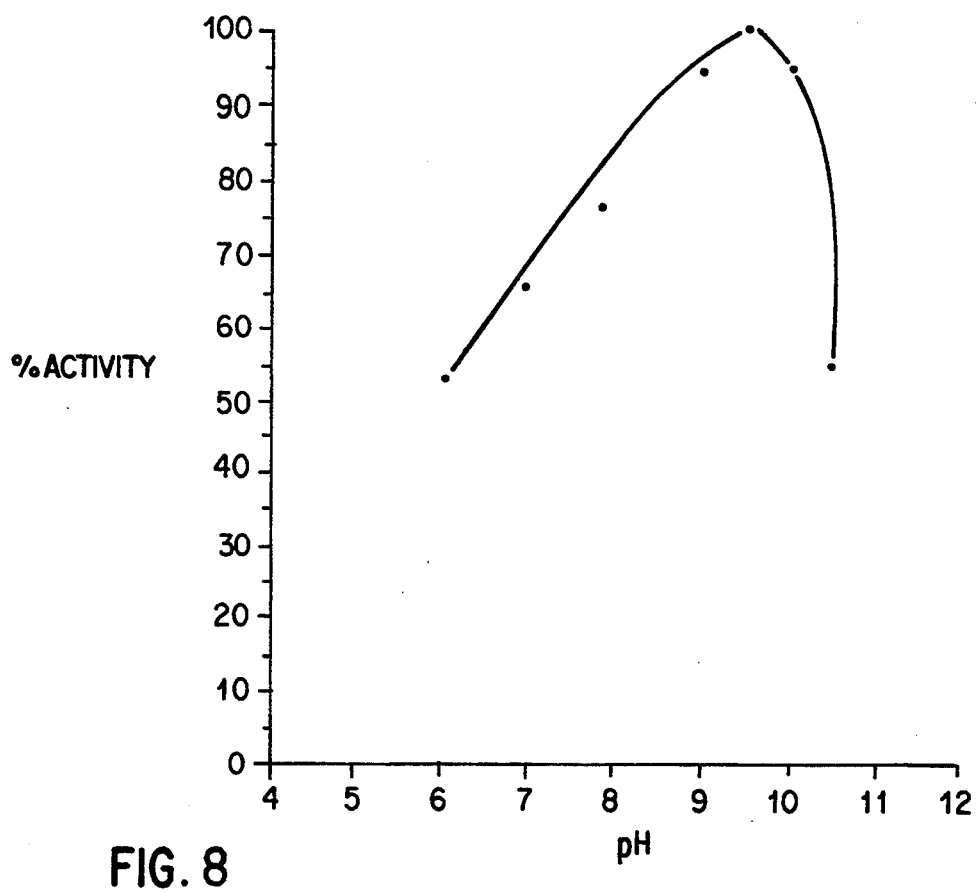
Figure 9:
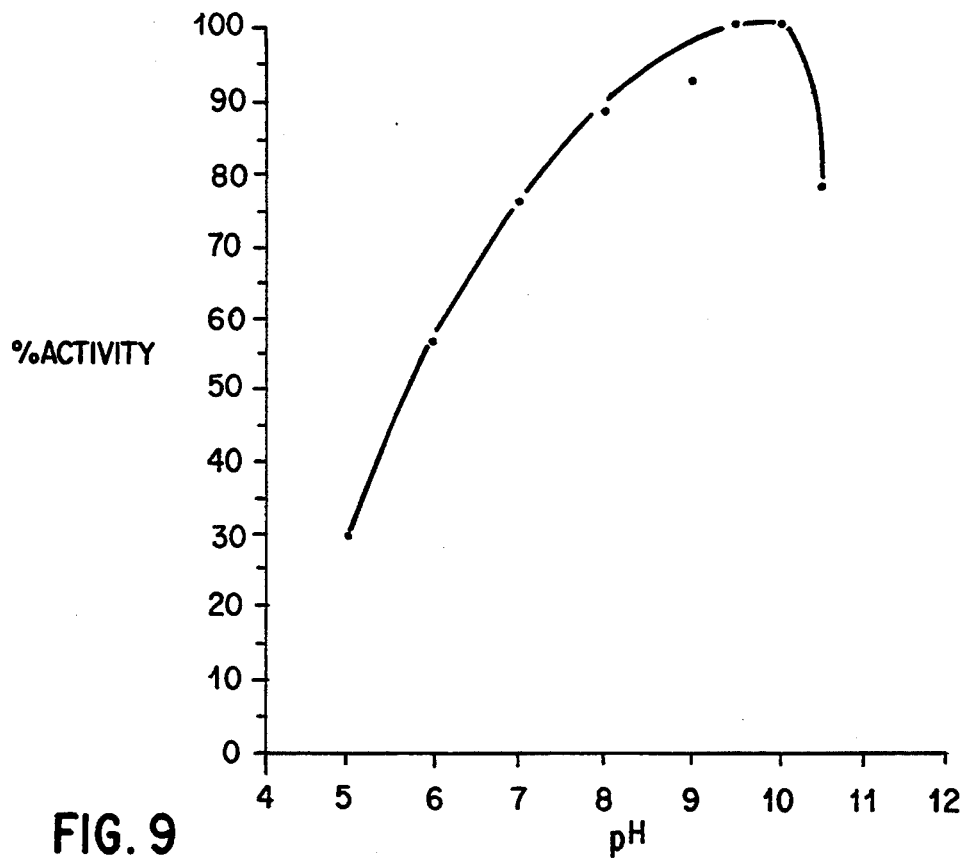
Figure 10:
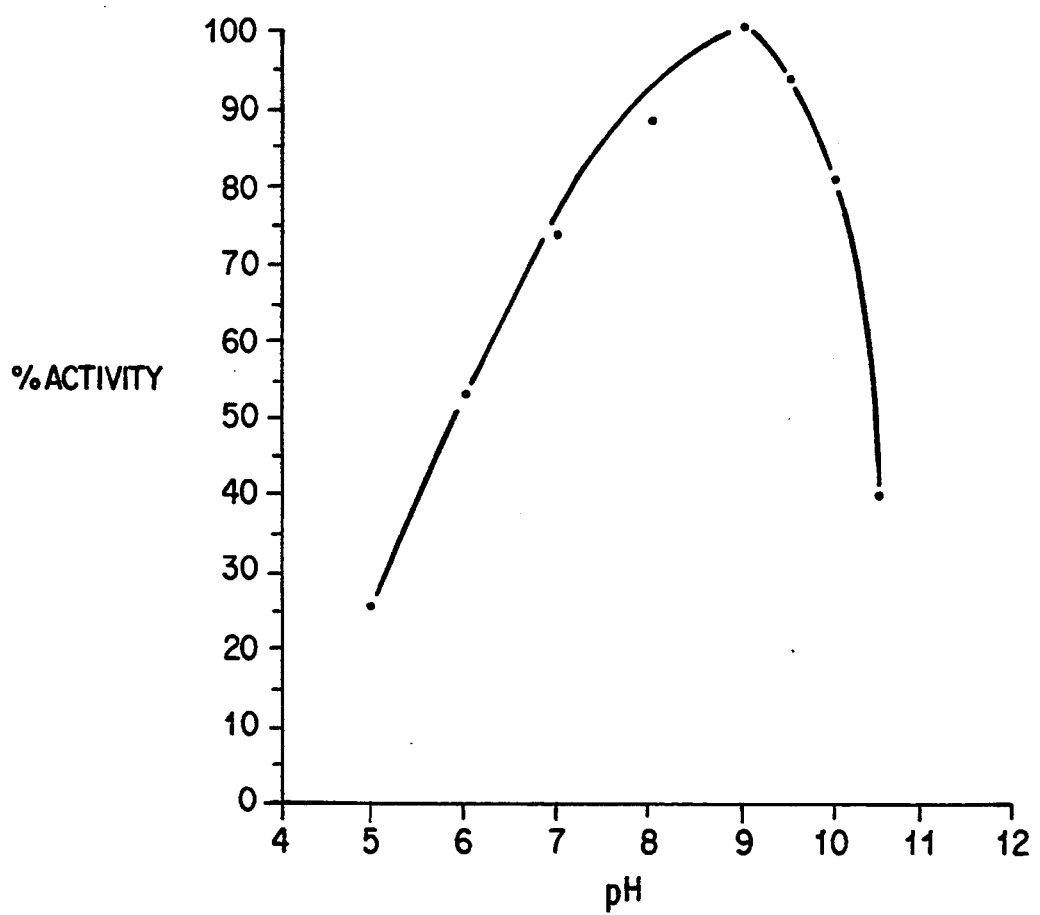

FIGS. 8 to 10: Curves for the pH optima of the *lipases* from *Bacillus pumilus* DSM 5776 FIG. 11), from *Bacillus pumilus* DSM 5777 (FIG. 9) and from *Bacillus pumilus* DMS 778 (FIG. 10).

Figure 11:
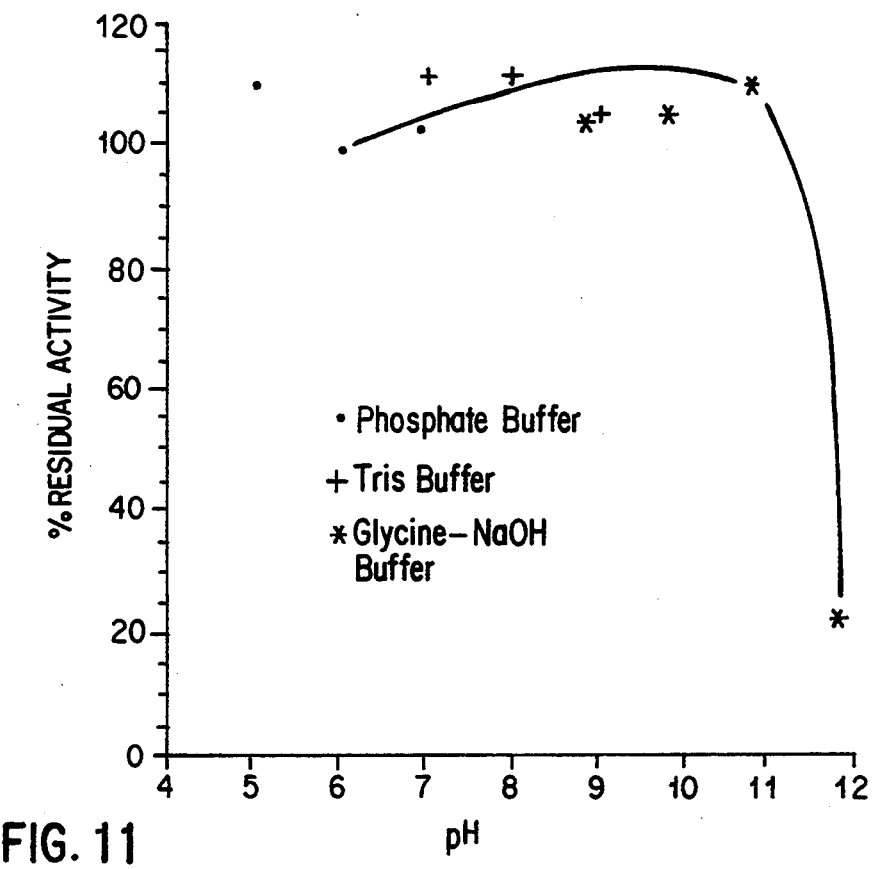
Figure 12:
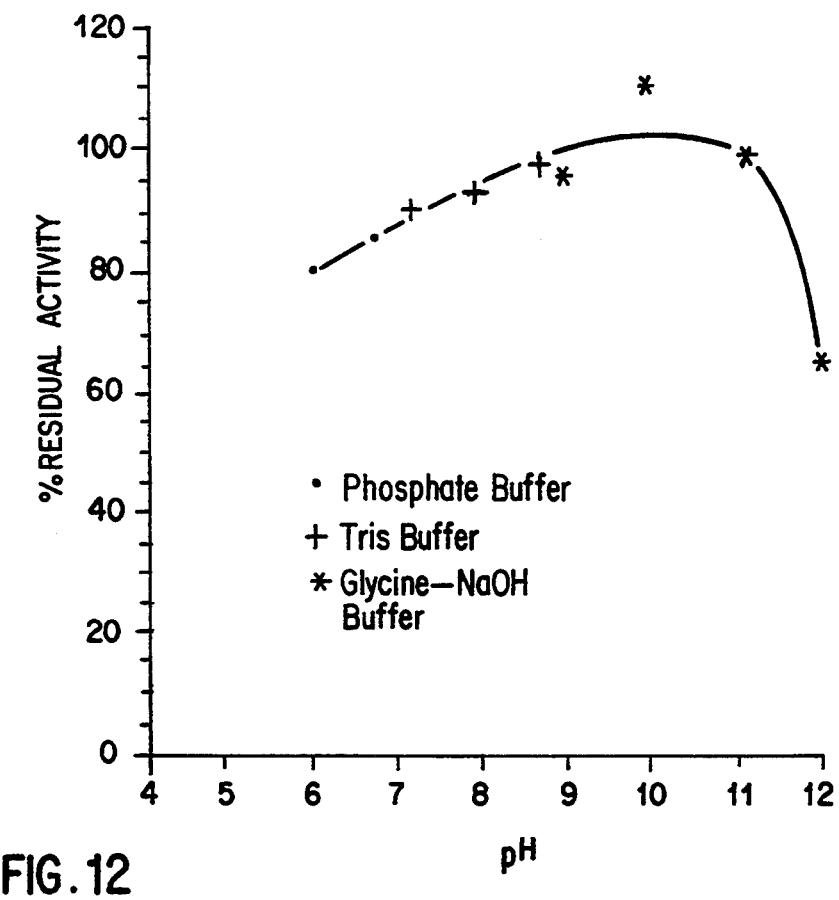
Figure 13:
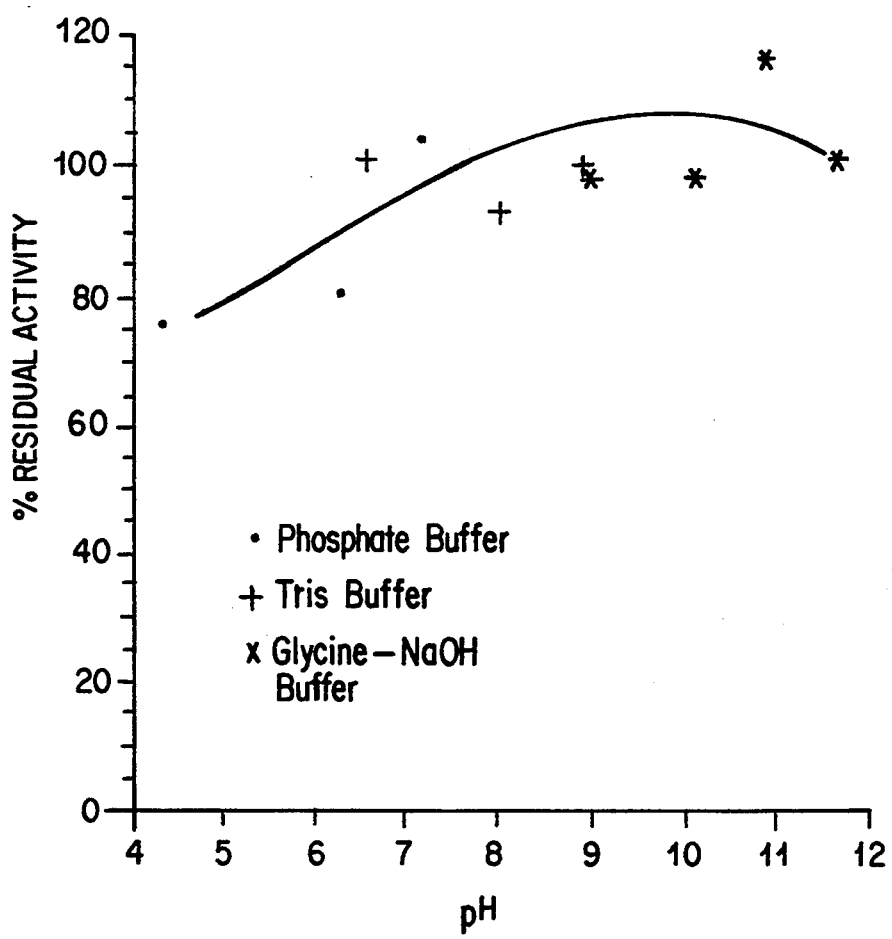

FIGS. 11 to 13: Curves of the pH Stability of the *lipases* from *Bacillus pumilus* DSM 5776 (FIG. 11), from *Bacillus pumilus* DSM 5777 (FIG. 12) and from *Bacillus pumilus* DSM 778 (FIG. 13). Phosphate buffer ('), tris-HCl buffer (+) and glycine-NaOH buffer (*) were used to adjust the pH.

Figure 14:
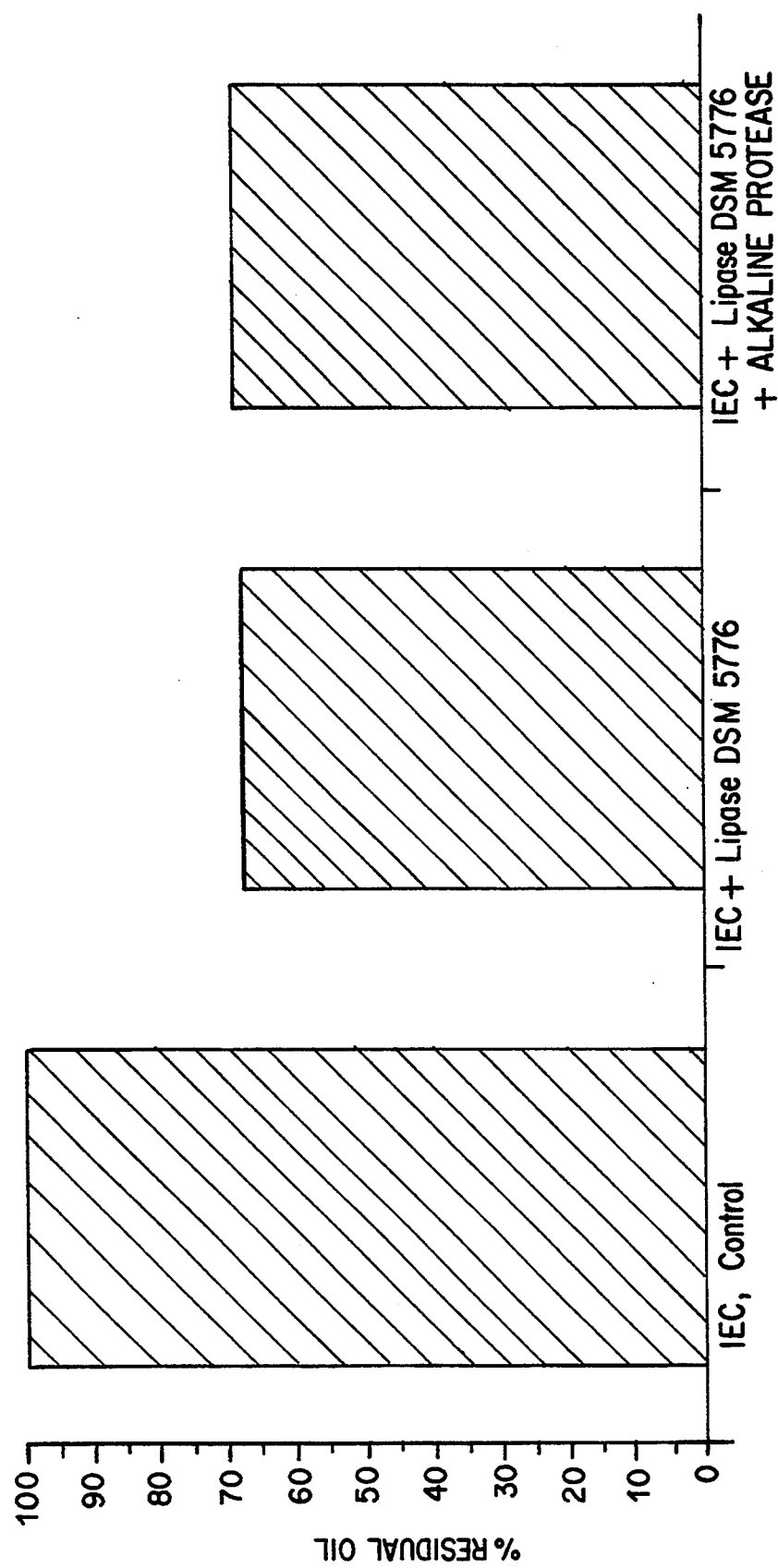
Figure 15:
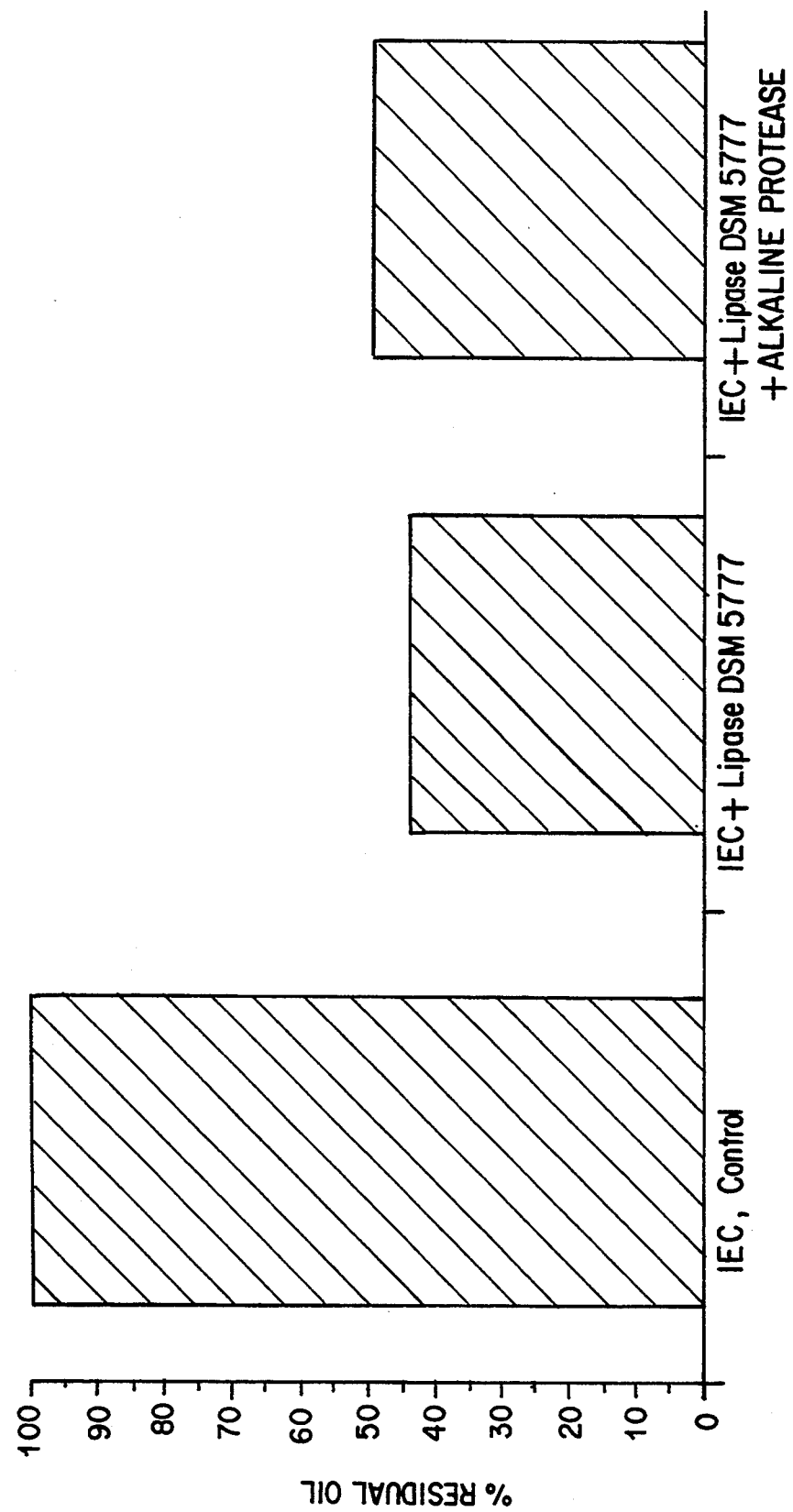
Figure 16:
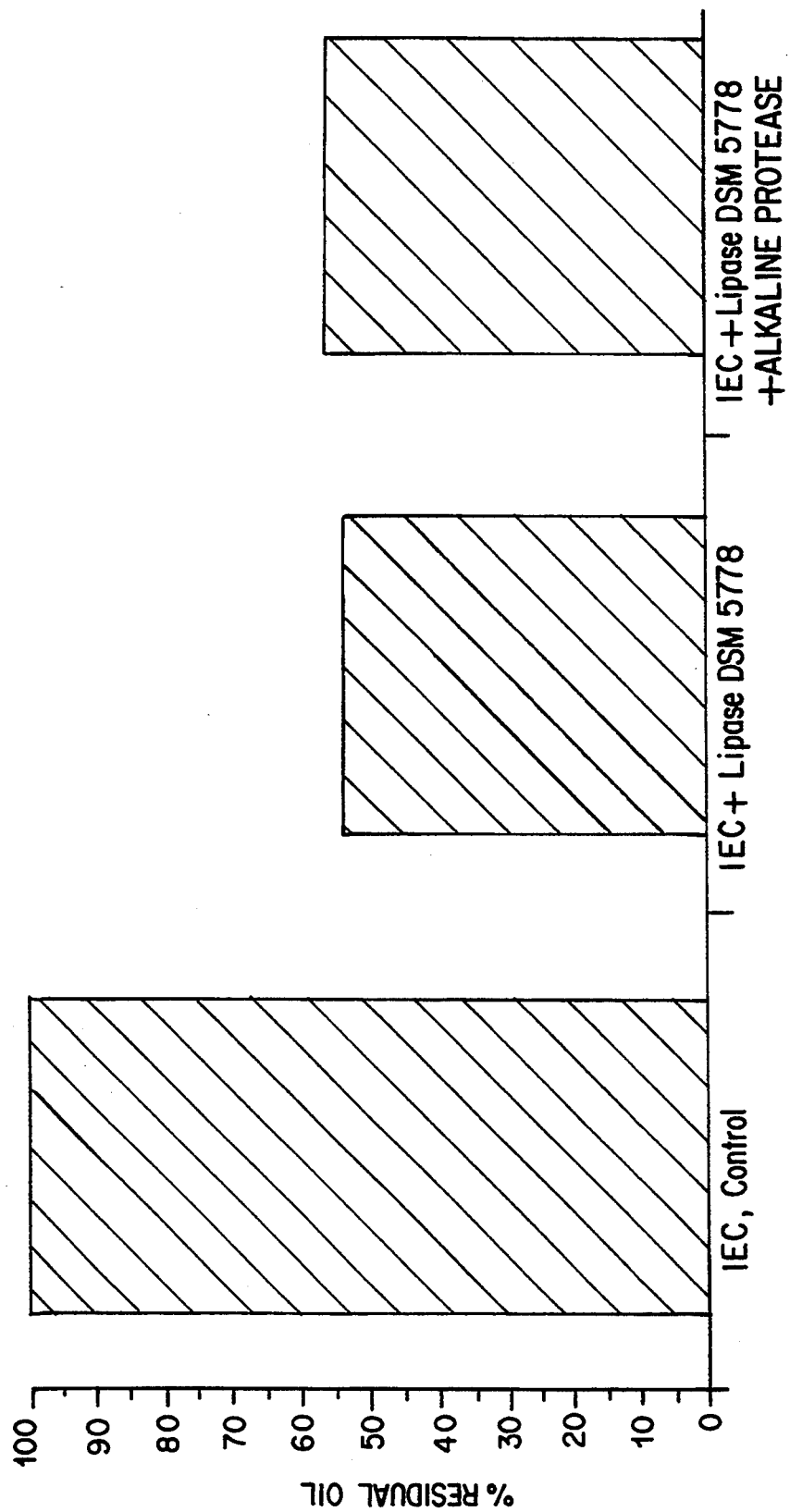

FIGS. 14 to 16: Graphic representation of the laundering effectiveness of *bacillus lipases* in an IEC standard detergent formulation, as well as in the presence of alkaline protease; laundering effectiveness of the lipase from *Bacillus pumilus* DSM 5776 (FIG. 14), from *Bacillus pumilus* DSM 5777 (FIG. 15) and from *Bacillus pumilus* DSM 5778 (FIG. 16).

EXAMPLES

The following disclosure gives typical embodiments of the invention by way of example and for the purpose of providing a further explanation of the invention without, however, limiting the scope of the invention.

To simplify the examples, some frequently recurring methods and concepts are described in greater detail in the following and then referred to in the individual examples only by an abbreviation. Unless stated otherwise, the methods described in Maniatis et al. (Maniatis et al.=T. Maniatis, E. E Fritsch, J. Sambrook, Molecular Cloning, A Laboratory Manual. Cold Spring Harbor Laboratory, 1982) were generally followed.

The various restriction endonucleases used belong to the state of the art and are commercially available. The reaction, cofactor and other conditions required whenever these known restriction endonucleases are used, are also known. For example, for an amount of about 1 µg of DNA, one unit (=1 U=unit) of the restriction endonuclease in about 20 µL of a buffer solution can be used. Adequate incubation times of about one hour at 37° C. were generally employed. However, the incubation conditions can be adapted to the given requirements. After incubation with a restriction endonuclease, the protein was removed by extraction (for example, with phenol and chloroform) and the cut DNA was isolated (for example, from the aqueous fraction by precipitation with ethanol) and thus made available for further use.

The cutting of DNA or vectors with restriction nucleases can optionally be followed by a hydrolysis of the terminal 5'-phosphate group with an alkaline phosphatase (dephosphorylation). It can thus be prevented that the end of the restricted vector, which is formed by the cutting, can recombine with itself. Such a recombination would prevent the desired insertion of a foreign DNA fragment in the restriction site. If a dephosphorylation of the 5' end was undertaken in the examples, it was done by a known procedure. Further details concerning the dephosphorylation reaction and the reagents required for this reaction may be found in Maniatis et al. (pages 133–134).

Partial hydrolysis means incomplete digestion of the DNA by means of a restriction endonuclease. The reaction conditions can be selected, so that some but not all of the sites, recognized by the restriction endonuclease used, are cut in a DNA substrate.

To extract and isolate certain DNA fragments, for example, after treatment of DNA with restriction endonuclease, the DNA fragments obtained were separated using a known procedure by means of gel electrophoresis (for example, on agarose gel) and subsequently identified by way of the molecular weight (determined by comparison with reference DNA fragments of known molecular weight). The desired DNA fragment was then removed from the corresponding gel zone.

Ligation refers to a method for forming phosphodiester bonds between DNA fragments (see, for example, Maniatis et al., page 146). Ligations can be carried out under known conditions, for example, in a buffer with about 10 units of T4 DNA ligase per 0.5 µg of the DNA fragments that are to be ligated.

Transformation is understood to be the infiltration of DNA into a microorganism, so that the DNA is replicated and expressed in this. For the transformation of *E. coli*, the calcium chloride method of Mandel et al. (1970, J. Mol. Biol. 53: 159) or of Maniatis et al. (pages 250 to 25 1) is, for example suitable. For *bacillus species*, the method of Anagnostopoulos et al. (1961, J. Bact. 81:741–746) is, for example, suitable.

In the enzyme stability data in the following examples, "completely stable" means a residual activity of at least 90% and "stable" means a residual activity of at least 80%.

The *bacillus* strains, isolated in Example 1, have been deposited on 2-7-1990 with the Deutschen Sammlung yon Mikroorganismen und Zellkulturen GmbH (DSM) (German Collection of Microorganisms and Cell Cultures GmbH) (address: Mascheroder Weg 1B, D-3300 Braunschweig) under the DSM numbers 5776, 5777 and 5778.

EXAMPLE 1

Isolation of Bacilli That Secrete Lipase

A) MMII medium (2% olive oil, 0.05% yeast extract, 0.1% NaCl, 0.5% $(NH_4)_2SO_4$, $MgSO_4 \times 2H_2O$, 0.2% urea, 10 mM sodium carbonate buffer of pH 9) was inoculated with a food sample (fresh cheese, stored for one week at room temperature) and incubated for 72 hours at 37° C. with shaking. Vegetative cells were killed by a 30minute treatment at 80° C. Various solutions of the culture, so treated, were streaked out on lipase screening plates, which contained 2.5% olive oil, 0.8% nutrient broth, 0.4% NaCl 2% agar, 0.001% rhodamine B and 10 mM sodium carbonate buffer (pH 9) (modified as described by Kouker and Jaeger, 1987, Appl. Environ. Microbiol. 53, pages 211–213). The plates were incubated at 37° C. After an incubation period of 2 days, orange-colored halos became visible under UV light around some colonies. One of these colonies was isolated and the isolated strain was deposited with the Deutschen Sammlung yon Mikroorganismen (German Collection of Microorganisms and Cell Cultures GmbH) under the number DSM 5776.

B) Butter, which had been stored for one week at room temperature, was pasteurized (30 minutes at 80° C.). With a sample of this, VMI medium (1% Tween 80, 1% tryprone, 0.5% yeast extract, 0.5% NaCl, 10 mM sodium carbonate buffer of pH 9) was inoculated and incubated for 48 hours at 37° C. with shaking. Various dilutions of the culture were streaked out on lipase-screening plates. After an incubation period of 2 days, an orange-colored halo became visible under UV light about one colony. This colony was isolated and the isolated strain was deposited with the Deutschen Sammlung von Mikroorganismen GmbH (German Collection of Microorganisms and Cell Cultures GmbH) under the number DSM 5777.

C) Lard, which had been stored for four days at room temperature, was pasteurized (30 minutes at 80° C.). A sample of this was used to inoculate VMII medium (1% Tween 80, 1% olive oil, 1% tryptone, 0.5% yeast extract, 0.5% NaCl, 10 mM sodium carbonate buffer of pH 9) and incubated for 48 hours at 37° C. with shaking. Various dilutions of the culture were streaked out on lipaseoscreening plates. After an incubation period of 2 days, orange-colored halos became visible under UV light around some colonies. One of these colonies was isolated and the isolated strain was deposited with the Deutschen Sammlung von Mikroorganismen GmbH (German Collection of Microorganisms and Cell Cultures GmbH) under the number DSM 5778.

EXAMPLE 2

Identification of the Bacilli Isolated in Example 1

The strains with the DSM numbers 5776, 5777 and 5778, which were isolated in Example 1, are gram-positive, spore-forming, aerobic microorganisms, which can be assigned to the *bacillus* genus. The cell morphology and the colony morphology are described in the following. Biochemical reactions and reactions to certain growth conditions are listed in Table 1.

Bacillus Species DSM 5776:

Rod-shaped bacterium with rounded corners. The gram reaction (gram staining, KOH test) is positive. After 2 days at 37° C. on TY agar (see below), the colonies have a diameter of 3.5 to 4 ram, are beige-colored and have a smooth to undulating edge. Occasionally, droplet formation is also observed on the colonies; the colonies can be glossy or dried out and wrinkled. On TY agar, the cells have a size of 0.7 to 0.9 $\mu m \times 1.2$ to 2.8 $\mu m$ and usually occur as single cells or as chains of two or three cells. The spores are oval and are positioned centrally to subterminally. The strain sporulates readily.

Bacillus Species DSM 5777

Rod-shaped bacterium with rounded corners. The gram reaction (gram staining, KOH test) is positive. After 2 days at 37° C. on TY agar (see below), the colonies have a diameter of 3.2 to 4.2 ram, are beige-colored and have a smooth to undulating edge. Occasionally, droplet formation is also observed on the colonies; the colonies can be glossy or dried out and wrinkled. On TY agar, the cells have a size of 0.8 to 0.9 $\mu m \times 1.2$ to 2.8 $\mu m$ and usually occur as single cells or as chains of two or three cells. The spores are oval and are positioned centrally to subterminally. The strain sporulates readily.

Bacillus Species DSM 5778

Rod-shaped bacterium with rounded corners. The gram reaction (gram staining, KOH test) is positive. After 2 days at 37° C. on TY agar (see below), the colonies have a diameter of 2.2 to 3 mm, are beige-colored and have a smooth to undulating edge. Occasionally, droplet formation is also observed on the colonies; the colonies can be glossy or dried out and wrinkled. On TY agar, the cells have a size of 0.7 to 0.9 $\mu m \times 1.3$ to 3.7 $\mu m$ and usually occur as single cells or as chains of two or three cells. The spores are oval and are positioned centrally to subterminally. The strain sporulates readily.

TY Aaar;

yeast extract: 5 g
$MgCl_2 * 6H_2O$: 8.75 g
$MnCl_2 * 6H_2O$: 0.016 g
agar: 16 g
doubly distilled water: to 1,000 mL
pH: 7.0±0.3

On the basis of the results obtained after carrying out the tests named in Table 1 (according to Bergeys Manual of Determinative Bacteriology, vol. 2, 1121–1125, P. H. A. Sneath (ed.), Williams and Wilkins, Baltimore-London-Los Angeles-Sydney, 1986), the strains isolated can be assigned to the *Bacillus pumilus* species. They deviate merely in a few characteristics (Voges-Proskauer Test, pH of the V-P nutrient solution and formation of egg yolk lecithinase, as well as in the case of the DSM 5777 strain, with respect to the growth in 7% NaCl) from the characteristics listed there for *Bacillus pumilus*.

*Bacillus pumilus* is an organism, which occurs everywhere and forms colonies of variable appearance on culture media. The strains, isolated according to Example 1, accordingly are Bacillus pumilus DSM 5776 (Example 1A),
Bacillus pumilus DSM 5777 (Example 1B) and
Bacillus pumilus DSM 5778 (Example 1C).

TABLE 1

| Characteristic | Bacillus DSM 5776 | DSM 5777 | DSM 5778 | pumilus |
|---|---|---|---|---|
| Cell Diameter > 1 μm | − | − | − | − |
| Spore Shape Round | − | − | − | − |
| Sporangium Swollen | − | − | − | − |
| Parasporal Crystals | − | − | − | − |
| Catalase | + | + | + | + |
| Anaerobic Growth | − | − | − | − |
| Voges-Proskauer Test | − | − | − | + |
| pH in V-P Nutrient Solution | | | | |
| <6 | | | | + |
| >7 | + | + | + | |
| Acid Formation on | | | | |
| Glucose | + | + | + | + |
| L-Arabinose | + | + | + | + |
| D-Xylose | + | + | + | + |
| D-Mannitol | + | + | + | + |
| Gas Formation with Glucose | − | − | − | − |
| Hydrolysis of | | | | |
| Casein | + | + | + | + |
| Gelatine | + | + | + | + |
| Starch | − | − | − | − |
| Metabolization of | | | | |
| Citrate | + | + | + | + |
| Propionate | − | − | − | − |
| Breakdown of Tyrosine | − | − | − | − |
| De-amination of Phenylalanine | | | | |

TABLE 1-continued

| Characteristic | Bacillus DSM 5776 | DSM 5777 | DSM 5778 | pumilus* |
|---|---|---|---|---|
| Egg yolk Lecithinase | + | + | + | − |
| Nitrate reduction to Nitrite | − | − | − | − |
| Formation of | | | | |
| Indole | − | − | − | − |
| Dihydroxyacetone | − | − | − | n.d. |
| NaCl— and KCl— Requirement | n.d. | n.d. | n.d. | − |
| Allantoin- or Ureate- Requirement | n.d. | n.d. | n.d. | − |
| Growth at pH - | | | | |
| 6.8 in NB | + | + | + | + |
| 5.7 in NB | + | + | + | + |
| Growth in NaCl | | | | |
| 2% | n.d. | n.d. | n.d. | + |
| 5% | + | + | + | + |
| 7% | + | − | + | + |
| 10% | − | − | + | n.d. |
| Growth at | | | | |
| 5° C. | n.d. | n.d. | n.d. | − |
| 10° C. | n.d. | n.d. | n.d. | + |
| 30° C. | + | + | + | + |
| 40° C. | n.d. | n.d. | n.d. | + |
| 50° C. | n.d. | n.d. | n.d. | d |
| 55° C. | n.d. | n.d. | n.d. | − |
| 65° C. | n.d. | n.d. | n.d. | − |
| Growth in the presence of Lysozyme | + | + | + | d |
| Autotrophic with $H_2 + CO_2$ or CO | n.d. | n.d. | n.d. | − |

*B. pumilus data from Bergeys Manual of Determinative Bacteriology, Vol. 2, p. 1123, P.H.A. Sneath, ed., Williams & Wilkins, Baltimore-London-Los Angeles-Sydney, 1986.
+ 90% or more positive
− 90% or more negative
d 11–89% positive
n.d. not determined
NB Nutrient Broth

EXAMPLE 3

Lipase Formation with the Natural Bacillus Isolates of Example 1

The DSM 5776, DSM 5777 and DSM 5778 *bacillus* strains, isolated in Example 1 and identified in greater detail in Example 2, were incubated at pH 9.0 and a temperature of 30° C. at 300 rpm in a medium of the following composition.

Composition of the medium: 20 g soybean flour, 10 g peptone, 10 g soluble starch, 2 g dipotassium hydrogen phosphate, 1 g magnesium sulfate heptahydrate, 5.88 g sodium hydrogen carbonate, 3.18 g sodium carbonate, 10 g Tween 80, doubly distilled water to 1,000 mL; the pH of the finished medium was 9.0±0.1.

After an incubation period of 22 hours for the DSM 5777 and 5778 *bacillus* strains and of 41.5 hours for the DSM 5776 *bacillus* strain, the cultures were freed from cell material by centrifuging for 15 minutes and the activity of the lipase contained in the supernatant solution of the culture was determined as described in Example 8. The following activities were measured. They show that the bacilli, isolated as described in Example 1, secrete *lipases*.

| Lipase from Bacillus | Activity |
|---|---|
| DSM 5776 | 8.5 U/mL |
| DSM 5777 | 10.3 U/mL |
| DSM 5778 | 12.8 U/mL |

EXAMPLE 4

Producing Genomic DNA Libraries from Natural Bacillus Isolates And Isolating Genes of Alkaline Bacillus Lipases From the natural isolates of *bacillus* DSM 5776, *bacillus* DSM 5777 and *bacillus* DSM 5778 of Example 1, the chromosomal DNA was isolated by the method of Saito et al. (1963, Biochim. Biophys. Acta, 72, pages 619–629) and partially hydrolyzed with the restriction endonucleases Sau3A. The restriction fragments were separated by electrophoresis on an agarose gel and those fractions were isolated, the size of which was 3 to 8 kilobases (KB).

The isolated fragments from the bacilli DSM 5776, DSM 5777 and DSM 5778, selected on the basis of size, were recombined with vector DNA of the plasmid pUB110, which had been prepared as described in Example 7.

For this purpose, the pUB110 plasmid was first restricted with the restriction endonuclease BamHI and subsequently dephosphorylated with alkaline phosphatase from calf intestines. Subsequently, 20 μg of the DNA fragments from the DSM 5776, DSM 5777 or DSM 5778 bacilli were incubated for 24 hours at 16° C. with 4 μg of the restricted and dephosphorylated vector DNA in a total volume of 200 μL with T4 DNA ligase.

With the respective recombined DNA obtained in vitro, protoplasts of the Bacillus subtilis PSL 1 strain (Bacillus Genetic Stock Center 1 A 510) were transformed by the method described by S. Chang and N. Cohen (1979, Mol. Gen. Genet. 168, pages 111–115). The transformants were selected on plates with neomycin and subsequently transferred to lipase screening plates (without sodium carbonate buffer). Of the approximately 100,000 transformants obtained, a few were found, which could be identified as lipase secreting transformants on the basis of the fluorescing halos around the respective colony.

From these clones, the respective plasmid DNA was isolated by the method of Maniatis et al. The cloned fragments from *bacillus* DSM 5776, *bacillus* DSM 5777 or *bacillus* DSM 5778, contained in these plasmids, contained (as demonstrated by Example 5) the complete, correct DNA sequence for the respective alkaline *bacillus lipase*. The plasmids with an insert from the DNA of the DSM 5776 *bacillus* strain received the name pL2-22-11, the plasmid with an insert from the DNA of the DSM 5777 *bacillus* strain received the name pL4-22-14 and the plasmid with an insert from the DNA of the DSM 5778 *bacillus* strain received the name pL11-8-20.

The plasmids were cut in each case with different restriction endonucleases, the restricted DNAs obtained were separated by electrophoresis on an agarose gel and provisional restriction cards for the lipase-carrying inserts in the above-described plasmids were set up with the help of the band pattern. The provisional sequence of identifying sites for restriction endonucleases, given in the following, was determined for the lipase gene-carrying inserts in the above-mentioned plasmids; for the insert in pL2-22-11 with a size of about 3.5 KB: ClaI, PvuII, NcoI, XbaI, XbaI, AcyI, PvuII, MluI, EcoRV, BclI, EcoRV; for the insert in pL4-23-14 with a size of about 2.6 KB: EcoRV, ClaI, NcoI, XbaI, AvaII, ClaI, BglII, XbaI, EcoRV; for the insert in pL11-8-20 with a size of about 1.7 KB: NcoI, AvaII, ClaI, XbaI, EcoRV.

EXAMPLE 5

Expression of the Lipase Gene, as well as Checking and Verifying the Lipolytic Activity of the Expressed Bacillus Lipases The pL2-22-11, pL4-23-14 and pLll-8-20 plasmids were introduced once more into the *B. subtilis* PSL 1 strain and the transformants obtained were cultured. Furthermore, the pL2-22-11 plasmid was introduced into the DSM 5776 *bacillus* strain, the pL4-23-14 plasmid was introduced into the DSM 5777 *bacillus* strain and the pL11-8-20 plasmid was introduced into the DSM 5778 *bacillus* strain and also cultured. As control strains, a *B. subtilis* PLS 1, which had not been transformed, a *B. subtilis* PSL1 transformed with the pUB110 plasmid, the starting strains for the isolation of the lipase genes, that is, the DSM 5776, DSM 5777 and DSM 5778 bacilli, as well as the transformants of these starting strains with the pUB 110 plasmid were also cultured. The transformation was carried out in each case by the method of S. Chang and N. Cohen, which is given in Example 4. For the culturing, *bacillus* strains transformed with the pL2-22-11, pL4-23-14 or pL11-8-20 plasmids and the control strains were incubated for 18 hours at 37° C. and 280 rpm in agitated flasks with 50 mL pre-culture medium (1.5% tryptone, 1% yeast extract, 2% starch). Agitated flasks with 50 mL of the main culture medium (1% Tween 80, 1% tryptone, 1% yeast extract, 4% starch and 2% soybean flour) were inoculated with 1.5 mL of this culture and incubated at 37° C. and 350 rpm. The media for all plasmid-containing strains additionally contained 10 μg of neomycin/mL. The media for the DSM 5776, DSM 5777 and DSM 5778 strains of bacilli, as well as their plasmid-containing derivatives additionally contained 10 mL of sodium carbonate buffer (1 molar, ph 9.75) per liter of medium.

After 48 hours, samples were taken from the cultures and centrifuged and the lipolytic activities in the supernatant solutions determined as described in Example 8. Table 2 shows the results of this activity determination.

TABLE 2

| Bacillus Strains | Activity (U/mL) |
|---|---|
| *B. subtilis* PSL 1 | <0.1 |
| *B. subtilis* PSL 1 (pUB110) | <0.1 |
| *B. subtilis* PSL 1 (pL2-22-11) | 5.3 |
| *B. subtilis* PSL 1 (pL4-23-14) | 7.2 |
| *B. subtilis* PSL 1 (pL11-8-20) | 6.4 |
| B. DSM 5776 | 4.8 |
| B. DSM 5776 (pUB110) | 4.5 |
| B. DSM 5776 (pL-22-11) | 112 |
| B. DSM 5777 | 6.2 |
| B. DSM 5777 (pUB110) | 5.9 |
| B. DSM 5777 (pL4-23-14) | 224 |
| B. DSM 5778 | 5.8 |
| B. DSM 5778 (pUB110) | 5.2 |
| B. DSM 5778 (pL11-8-20) | 153 |

EXAMPLE 6

Sequencing the Structure Genes for the Bacillus Lipases from the Bacilli with the DSM Numbers 5776, 5777 and 5778

Plasmids with the inserts from the DNA of the bacilli DSM 5776, DSM 5777 and DSM 5778, carrying the respective lipase gene, were restricted in each case with various restriction endonucleases. For each of the three lipase-carrying inserts, one group of fragments was obtained in this manner, from which the respective smallest fragment, which still exhibited lipase activity, was subcloned in a manner customary in the art with the help of *Bacillus subtilis* PSL1 as host. The plasmids obtained contained in each case lipase gene-carrying insert fragments of about the following sizes: for *bacillus* DSM 5776, an approximately 1.45 KB DNA fragment; for *bacillus* DSM 5777, an approximately 1.38 KB DNA fragment; for *bacillus* DSM 5778, an approximately 1.09 KB DNA fragment.

The above-obtained plasmids with the lipase gene-carrying fragments were used for the sequencing of the structure genes, which is described in the following. For this purpose, the lipase gene-carrying fragments were cut out of the respective plasmids by cutting with restriction endonucleases and brought into the phagemids pBS (+) or pBS(−) for producing single stranded DNA; the phagemids pBS (+/−) were purchased from Stratagene (La Jolla, California). The nucleotide sequences of the lipase genes, contained in the isolated single-stranded phagemids, was determined using methods known in the art, such as the dideoxy chain terminator method of Sanger et al. (1977, Proc. Natl. Acad. Sci. USA 74:5463) or the method of base-specific chemical splitting of single DNA strands of Maxam et al. (1980, in Methods in Enzymology, L. Grossmann, K. Modave, eds., Academic Press Inc., New York and London, vol. 65, 499). The nucleotide sequence, determined for the DNA fragment from *bacillus* DSM 5776 and the assigned amino acid sequence of the lipase is shown in FIG. 1 and in SEQ ID NOS. 1 and 2. The start of the amino acid sequence of the mature lipase was determined by the amino acid sequencing of the N-terminal end of the lipase. The DNA sequences and the associated amino acid sequences for the lipase gene from *bacillus* DSM 5777 and DSM 5778 were determined similarly.

The amino acid sequence of the lipase from *bacillus* DSM 5777 differs from the amino acid sequence of FIG. 1 (SEQ ID NO:2) only in position 149, in which there is the amino acid Val instead of Ile. It is therefore more than 99% homologous with the amino acid sequence of FIG. 1 (SEQ ID NO:2).

The amino acid sequence of the lipase from *bacillus* DSM 5778 differs from the amino acid sequence of FIG. 1 (SEQ ID NO:2) only in 7 positions as follows: in position 20, there is the amino acid Tyr instead of Phe; in positions 27-28, there are the amino acids Val-Gly instead of Ala-Thr; in positions 57 and 147 there is the amino acid Lys instead of Arg; in the positions 149-150, there are the amino acids Val-Gln instead of Ile-Leu. The amino acid sequence of the lipase from *bacillus* DSM 5778 therefore is more than 96% homologous with the amino acid sequence of FIG. 1 (SEQ. ID NO:2).

EXAMPLE 7

Isolation and Purification of the Plasmid puB110

From the *Bacillus subtilis* BD366 strain (Bacillus Genetic Stock Center 1 E 6) the plasmid pUB110 was isolated by the method of T. J. Gryczan et al. (1978, J. Bacteriol. 134:319–329) and subsequently purified by cesium chloride density gradient centrifugation by the method of Maniatis et al. (page 93). The vector pUB110 contains a restriction site for the restriction endonuclease BamHI. This restriction site occurs only once. As marker, the vector pUB 110 contains a DNA sequence, which codes for antibiotic resistance to neomycin as well as for the replication of DNA sequences required in *bacillus species* (origin of replication).

EXAMPLE 8

Determination of the Activity of *Bacillus lipases*

Lipases are triacylglycerol-acyl hydrolases of the E.C.3.1. class (class according to the Enzyme Commission classification), which hydrolyze emulsified triglycerides of long-chain fatty acids. The site of the lipase actin is the interface between the oil droplets and the aqueous phase. By these means, *lipases* can be differentiated unambiguously from esterases, which convert water-soluble substances. Admittedly, *lipases* can also split water-soluble substrates; however, the effect of the interfacial surfaces of emulsified triglycerides on the reaction is clear. Consequently, the substrate concentration for *lipases* is given in $m^2/L$ and not in moles/L. The degree of emulsification of the substrate, as well as the reproducible production of the substrate emulsion is of decisive importance for the test of lipase activity. As emulsifiers, particularly gum arabic, polyvinyl alcohol or sodium deoxycholate, for example are used.

The reaction product of the hydrolysis, the free fatty acid, is usually determined titrimetrically. Of the large number of known titrimetric methods, a direct, continuous titration under steady pH conditions during the reaction was carried out here. In carrying out this continuous, titrimetric test, it should be noted that, when long-chain triglycerides are used as substrate, the apparent protolysis constant $pK_a$ of long-chain triglycerides lies at a pH of about 9. If measurements are carried out at lower pH values only a small portion of the product formed is determined titrimetrically. The apparent $pK_a$ value can be affected by the addition of sodium chloride.

DESCRIPTION OF THE ACTIVITY TEST

Substrate emulsion: 10 g triolein, 10 g gum arabic, 100 mL of doubly distilled water. The emulsion was emulsified with a laboratory mixer for 15 minutes at a high rpm.

Buffer: 100 mM sodium chloride, 20 mM calcium chloride dihydrate.

Caustic solution: 10 mM sodium hydroxide solution.
Temperature: 30° C.

Constant pH apparatus: consisting of a pH meter, control equipment, metering pump and recording equipment for the consumption of sodium hydroxide solution.

METHOD

Buffer solution (20 mL) is added to 10 mL of the substrate emulsion and heated to 30° C. The pH of this mixture is then adjusted to 9.5. Subsequently, 0.2 to 0.5 mL of the sample or of the blank solution (which has the same composition as the sample, but without active lipase; before the determination of the activity, the sample is inactivated thermally) are added and the pH is kept constant at 9.5 by titration with sodium hydroxide solution. For the entire duration of the experiment, the consumption of sodium hydroxide solution was recorded. Under the given conditions, one unit (U) of lipase activity brings about the release of 1 $\mu$mole of fatty acid per minute.

EXAMPLE 9

Determination of the Enzyme Characteristics of Bacillus Lipases

To determine the enzyme characteristics such as temperature optimum, temperature stability, pH optimum and pH stability, the supernatant solutions obtained by culturing bacilli were centrifuged for 30 minutes at 100,000 the acceleration due to gravity, in order to separate the cells of bacilli in the supernatant solution of the culture. The clear supernatant solution, obtained by centrifugation, was used for the following measurements, which are described under A) to D).

a) The temperature optimum of the *lipases* contained in the supernatant solutions of the cultures were determined with the help of the activity test described in Example 8. For this purpose, the temperature was varied in the range from 20° to 50° C. The results are shown in Table 3, as well as in FIGS. 2, 3 and 4.

The temperature optimum of the lipase from *bacillus* DSM 5776 is at 30° C. (FIG. 2).

The temperature optimum of the lipase from *bacillus* DSM 5777 is approximately at 40° C. (FIG. 3).

The temperature optimum of the lipase from *bacillus* DSM 5778 is at 30° C. (FIG. 4).

TABLE 3

| Alkaline Lipase from Bacillus | Lipase Activity in % as a Function of Temperature in °C. | | | | |
|---|---|---|---|---|---|
| | 20 | 24 | 30 | 40 | 50 |
| DSM 5776 | 66.8 | — | 100 | 74.9 | 5.3 |
| DSM 5777 | — | 81.2 | 90.4 | 100 | 15.9 |
| DSM 5778 | 64.7 | — | 100 | 68.4 | 3.2 |

B) for the determination of the temperature stability, the lipase containing supernatant solutions were incubated for 30 minutes at different temperatures and the residual reactivity was determined subsequently by the method given in Example 8 for the activity determination. The results are shown in Table 4 and in FIGS. 5, 6 and 7.

The lipase from *bacillus* DSM 5776 is stable up to 40° C. After an incubation for 30 minutes at 50° C., it still shows a residual activity of 16.1% (FIG. 5).

It was observed that the lipase from *bacillus* DSM 5777 is stable up to 40° C. and at 50° C. still has a residual activity of 21.3% (FIG. 6).

The lipase from *bacillus* DSM 5778 is stable up to 40° C. and, after being incubated for 30 minutes at 50° C., still has a residual activity of 22.5% (FIG. 7).

TABLE 4

| Alkaline Lipase incubation from Bacillus | Residual Lipase Activity in % as a Function of Temperature in °C. | | | | |
|---|---|---|---|---|---|
| | 30 | 40 | 50 | 60 | 70 |
| DSM 5776 | 105 | 100 | 16 | 2 | 2 |
| DSM 5777 | 96 | 102 | 22 | 9 | — |
| DSM 5778 | 95 | 90 | 24 | 0 | — |

C) To determine the pH optimum of the *bacillus lipases*, the activity determination, described in Example 8, was carried out at different pH values. However, because of the difficulty of determining the product of the enzymatic reactions at a pH below 9, the titration to a pH of 9.5 was not carried out continuously here, but was conducted at the end of the reaction time. The results are shown in Table 5 and in FIGS. 8, 9 and 10.

The optimum pH of the alkaline lipase from *bacillus* DSM 5776 is 9.5. At a pH of 10, the activity is still better than 90% (FIG. 8).

The optimum pH of the alkaline lipase from *bacillus* DSM 5777 is about 10 (FIG. 10).

The optimum pH of the alkaline lipase from *bacillus* DSM 5778 is 9. However, even at a pH of 10, 80% of the maximum activity is still present (FIG. 10).

TABLE 5

| Alkaline Lipase from Bacillus | Lipase Activity in % as a Function of the pH | | | | | | | | |
|---|---|---|---|---|---|---|---|---|---|
| | 5 | 6 | 7 | 7.8 | 8 | 9 | 9.5 | 10 | 10.5 |
| DSM 5776 | — | 53 | 65 | 76 | — | 95 | 100 | 95 | 55 |
| DSM 5777 | 30 | 56.8 | 76 | — | 88 | 92.2 | 99.8 | 100 | 78 |
| DSM 5778 | 25 | 53 | 73 | — | 88 | 100 | 93.5 | 80 | 40 |

D) For investigating the pH stability, the *lipases* were incubated for 21 hours at 4° C. in buffers of different pH values. Subsequently, the residual activity of the *lipases* was determined as described in Example 8. For the pH 5 to pH 7 range, phosphate buffer was used, for the pH 7 to pH 9 range, tris-HCl buffer (=tris(hydroxymethyl)aminomethane buffer) was used and, for the pH 9 to pH 12.8 range, glycine/sodium hydroxide buffer was used. The results are shown in FIGS. 11, 12 and 13.

The enzyme from *bacillus* DSM 5776 is completely stable within a pH range from 5 to 11; after a 21-hour incubation period at pH=12, a residual activity of 22% is still present (FIG. 11).

The lipase from *bacillus* DSM 5777 is stable in the pH range from 6 to 11 (FIG. 12).

The lipase from *bacillus* DSM 5778 is completely stable in the pH range from 6.5 to 11.5 (FIG. 13).

EXAMPLE 10

Laundering Trials

The laundering effectiveness of the *Bacillus lipases* from the bacilli DSM 5776, DSM 5777 and DSM 5778 was investigated by laundering trials at low laundering temperatures in a standard detergent composition. The results show that the inventive *bacillus lipases* are outstandingly suitable for use in detergents even at low laundering temperatures, at which conventional detergents hardly remove any oil and fat contamination from fabric being washed.

A) Test Fabric

The suitability of enzymes for use in detergents is generally checked by laundering tests. Special test fabrics are commercially available for this purpose, for example, from the Eidgenoessischen Materialpruefungs- und Versuchsanstalt in St. Gallen (Switzerland), EMPA. The fabrics sold by EMPA are, however, primarily intended for testing detergent proteases. Therefore, to test detergent *lipases*, specially prepared test fabrics had to be produced, for example, by soiling the test fabric partly with oil or with a mixture of pigments, proteins and oil or also by impregnating the whole of the test fabric with oil, such as olive oil.

For the subsequent laundering trials, cotton fabrics were saturated with olive oil (extra virgin) and then freed from excess oil. The fabric was subsequently dried at 30° C. To inhibit ageing of the oil contamination, the fabric, so obtained and soiled with oil, was stored before use in an atmosphere of nitrogen at 4° C.

B) Laundering Trials Procedure

For the laundering tests, the test fabrics, prepared under A) of this example, were cut into pieces of suitable size, for example 5 cm × 5 cm. These small pieces of test fabric were washed at a temperature of 40° C. for 30 minutes in a Linitest washing machine, each with 100 mL of washing liquor consisting of perborate-containing IEC test detergent (with a concentration of 6 g/L) of the following composition.

Composition of the perborate-containing IEC test detergent, type 1 (Lever Sunlicht GmbH, Mannheim): 6.4 percent by weight linear alkyl sulfonates, 2.3 percent by weight ethoxylated fatty alcohols with 14% ethoxy groups, 2.8 percent by weight of sodium soap, 35 percent by weight sodium tripolyphosphate, 6 percent by weight sodium silicate, 1.5 percent by weight magnesium silicate, 1 percent by weight carboxymethylcellulose, 0.2 percent by weight ethylenediaminetetraacetic acid (EDTA), 0.2 percent by weight optical brightener (stilbene type), 16.8 percent by weight sodium sulfate and 7.8 percent by weight water, as a spray-dried powder without bleaching activator, as well as with 20 percent by weight sodium perborate tetrahydrate.

The laundering was carried out in water with 15 ° dH (German degrees of hardness). The fabric was subsequently subjected to a rinsing process with tap water. In each case, 5 such washing cycles were carried out. At the end of the entire washing process, the small pieces of test fabric were rinsed once again with tap water and the still adhering residual oil was subsequently extracted with chloroform. The residual oil, obtained in this way, was determined gravimetrically. This is an excellent method for establishing differences between the *lipases* and to ascertain whether and how well they are suitable for use in detergents. To some of the washing liquors, an alkaline detergent protease was added in addition in order to thus show, at the same time, the laundering effectiveness and the stability of the *bacillus lipases* in the presence of the protease. The activity of the protease used in the washing liquor in each case was 5 DU/mL (DU=Delft unit). The activity of the lipase used in the washing liquor is given in the following in conjunction with the results:

Laundering trials with the alkaline *bacillus lipase* from Bacillus DSM 5776 with a lipase concentration in the washing liquor of 60 U/mL (see also FIG. 14):

| Washing liquor | Residual Oil in % by weight |
|---|---|
| IEC test detergent (control) | 100 |
| IEC test detergent + lipase | 54.5 |
| IEC test detergent + lipase + alkaline protease | 57.0 |

Washing trials with the alkaline *bacillus lipase* from *bacillus* DSM 5777 with a lipase concentration in the washing liquor of 45 U/mL (see also FIG. 15):

| Washing Liquor | Residual Oil in % by weight |
|---|---|
| IEC test detergent (control) | 100 |
| IEC test detergent + lipase | 44.9 |
| IEC test detergent + lipase + alkaline protease | 50.0 |

Washing trials with the alkaline *bacillus lipase* from *bacillus* DSM 5778 with a lipase concentration in the washing liquor of 55 U/mL (see also FIG. 16):

| Washing Liquor | Residual Oil in % by weight |
| --- | --- |
| IEC test detergent (control) | 100 |
| IEC test detergent + lipase | 54.5 |
| IEC test detergent + lipase + alkaline protease | 57.0 |

The results show that the inventive *bacillus lipases* are outstandingly suitable for use in detergents. The inventive *lipases* lower the residual oil content to a value appreciably below that obtained with the control and their laundering effectiveness is not affected negatively even by the presence of an alkaline detergent protease.

EXAMPLE 11

Stability of the *Bacillus lipases* in Washing Liquor With and Without the Addition of Alkaline Detergent Protease For proof of the stability of the inventive *lipases* in washing liquors with and without the addition of alkaline detergents proteases, laundering trials were carried out as in Example 10. The activity of the lipase was determined as in Example 8 at the start of the laundering process (t=0) and at the end of the laundering process (t=30 minutes). The relative residual activity of the *lipases*, that is, the activity of the *lipases* at the end of the laundering process as a percentage of the initial activity at t=0, is given in the following.

| Washing Liquor | Relative Residual Activity in % |
| --- | --- |
| Lipase from *bacillus* DSM 5776 | 50.5 |
| Lipase from *bacillus* DSM 5776 + alkaline protease | 47.0 |
| Lipase from *bacillus* DSM 5776 | 69.4 |
| Lipase from *bacillus* DSM 5776 + alkaline protease | 65.5 |
| Lipase from *bacillus* DSM 5776 | 49.9 |
| Lipase from *bacillus* DSM 5776 + alkaline protease | 42.3 |

The results show that the inventive alkaline *bacillus lipases* have very good stability in washing liquors, even in the presence of proteases. The inventive *lipases* therefore are very suitable for use in detergent compositions, particularly also in protease-containing detergent compositions.

We claim:

1. An isolated lipase having a pH optimum in the alkaline pH range, a temperature optimum in the range from 30° to 40° C. and an amino acid sequence which is more than 96% homologous with the amino acid sequence given in FIG. 1 (SEQ ID NO: 2) obtainable by culturing Bacillus pumilus DSM 5776, Bacillus pumilus DSM 5777 or Bacillus pumilus DSM 5778.

2. An isolated lipase according to claim 1, wherein said lipase has the following properties:
   (1) Effect: breakdown of triglycerides and fatty esters;
   (2) pH optimum: at a pH of about 9 to 10;
   (3) pH stability: completely stable at a pH from 6.5 to 11, and retains a residual activity of at least 90% after incubation at a pH of 11 and a temperature of 4° C. for 21 hours;
   (4) Temperature optimum: at a temperature of about 30° to 40° C.;
   (5) Temperature stability: no significant effect on activity after incubation for 30 minutes at temperatures up to 40° C., and retains a residual activity of at least 90% after incubation for 30 minutes at 40° C.

3. An isolated DNA sequence coding for an alkaline Bacillus lipase having an amino acid sequence which is more than 96% homologous with the amino acid sequence of FIG. 1 (SEQ ID NO:2).

4. A purified culture of a Bacillus pumilus selected from the group consisting of Bacillus pumilus DSM 5776, *Bacillus pumilus* DSM 5777 and Bacillus pumilus DSM 5778.

5. A cleaning composition comprising an alkaline Bacillus lipase according to claim 1, and at least one conventional surface active detergent ingredient.

6. A cleaning composition according to claim 5, further comprising a protease enzyme.

7. A cleaning composition according to claim 5, wherein said composition is a detergent formulated for washing temperatures in the range from 30° and 40° C.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 793 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bacillus pumilus DSM 5776
        ( B ) STRAIN: DSM 5776

( i x ) FEATURE:
        ( A ) NAME/KEY: sig_peptide
        ( B ) LOCATION: 126..221

( i x ) FEATURE:
        ( A ) NAME/KEY: mat_peptide
        ( B ) LOCATION: 222..764

( i x ) FEATURE:
        ( A ) NAME/KEY: CDS
        ( B ) LOCATION: 126..764

( x i ) SEQUENCE DESCRIPTION: SEQ ID NO:1:

```
CCAAGGTGCT  TTTTGATTAT  TTATATTTTT  GTAAAATCAT  CTCATAAACA  TTACCTTGTT        60

CACTTTTCTG  ACATATTTTT  CTTGTATAAA  ATAGAGTCGT  ATAAGATGAA  TAAGGGGGAA       120

TGAAA  GTG ATT TTT GTT  AAG AAA AGG AGT  TTG CAA ATT CTC ATT GCG            167
       Val Ile Phe Val  Lys Lys Arg Ser  Leu Gln Ile Leu Ile Ala
       -32      -30              -25                    -20

CTT GCA TTG GTG ATT  GGT TCA ATG GCG  TTT ATC CAG CCG AAA GAG GCG            215
Leu Ala Leu Val Ile  Gly Ser Met Ala  Phe Ile Gln Pro Lys Glu Ala
            -15               -10                      -5

AAG GCG GCT GAG CAT  AAT CCG GTT GTG  ATG GTG CAC GGC ATT GGC GGT            263
Lys Ala Ala Glu His  Asn Pro Val Val  Met Val His Gly Ile Gly Gly
```

|   |   |   |   |   |   |   |   |   |   |   |   |   |   |   |   |     |
|---|---|---|---|---|---|---|---|---|---|---|---|---|---|---|---|-----|
|   | 1 |   |   |   | 5 |   |   |   |   | 10|   |   |   |   |   |     |
| GCC | TCT | TAT | AAC | TTT | TTT | TCT | ATT | AAA | AGT | TAT | TTG | GCC | ACA | CAA | GGC | 311 |
| Ala | Ser | Tyr | Asn | Phe | Phe | Ser | Ile | Lys | Ser | Tyr | Leu | Ala | Thr | Gln | Gly |     |
| 15  |     |     |     |     | 20  |     |     |     |     | 25  |     |     |     |     | 30  |     |
| TGG | GAT | CGA | AAC | CAA | TTA | TAT | GCT | ATT | GAT | TTC | ATA | GAC | AAA | ACA | GGA | 359 |
| Trp | Asp | Arg | Asn | Gln | Leu | Tyr | Ala | Ile | Asp | Phe | Ile | Asp | Lys | Thr | Gly |     |
|     |     |     |     | 35  |     |     |     |     | 40  |     |     |     |     | 45  |     |     |
| AAT | AAC | CGC | AAC | AAT | GGT | CCG | CGT | CTA | TCG | AGA | TTC | GTC | AAA | GAT | GTG | 407 |
| Asn | Asn | Arg | Asn | Asn | Gly | Pro | Arg | Leu | Ser | Arg | Phe | Val | Lys | Asp | Val |     |
|     |     |     | 50  |     |     |     |     | 55  |     |     |     |     | 60  |     |     |     |
| TTA | GAC | AAA | ACG | GGT | GCC | AAA | AAA | GTA | GAT | ATT | GTG | GCT | CAT | AGT | ATG | 455 |
| Leu | Asp | Lys | Thr | Gly | Ala | Lys | Lys | Val | Asp | Ile | Val | Ala | His | Ser | Met |     |
|     |     | 65  |     |     |     |     | 70  |     |     |     |     | 75  |     |     |     |     |
| GGC | GGA | GCG | AAC | ACG | CTA | TAC | TAT | ATC | AAG | AAT | CTA | GAT | GGC | GGC | GAT | 503 |
| Gly | Gly | Ala | Asn | Thr | Leu | Tyr | Tyr | Ile | Lys | Asn | Leu | Asp | Gly | Gly | Asp |     |
|     | 80  |     |     |     |     | 85  |     |     |     |     | 90  |     |     |     |     |     |
| AAA | ATT | GAG | AAC | GTT | GTC | ACA | ATT | GGT | GGA | GCA | AAC | GGA | CTC | GTT | TCA | 551 |
| Lys | Ile | Glu | Asn | Val | Val | Thr | Ile | Gly | Gly | Ala | Asn | Gly | Leu | Val | Ser |     |
| 95  |     |     |     |     | 100 |     |     |     |     | 105 |     |     |     |     | 110 |     |
| AGC | AGA | GCA | TTA | CCA | GGC | ACA | GAT | CCA | AAT | CAA | AAA | ATT | CTT | TAC | ACA | 599 |
| Ser | Arg | Ala | Leu | Pro | Gly | Thr | Asp | Pro | Asn | Gln | Lys | Ile | Leu | Tyr | Thr |     |
|     |     |     |     | 115 |     |     |     |     | 120 |     |     |     |     | 125 |     |     |
| TCC | GTC | TAT | AGC | TCA | GCA | GAT | CTT | ATT | GTC | GTC | AAC | AGC | CTC | TCT | CGT | 647 |
| Ser | Val | Tyr | Ser | Ser | Ala | Asp | Leu | Ile | Val | Val | Asn | Ser | Leu | Ser | Arg |     |
|     |     | 130 |     |     |     |     | 135 |     |     |     |     | 140 |     |     |     |     |
| TTA | ATT | GGC | GCA | AGA | AAC | ATC | CTG | ATC | CAT | GGC | GTT | GGT | CAT | ATC | GGT | 695 |
| Leu | Ile | Gly | Ala | Arg | Asn | Ile | Leu | Ile | His | Gly | Val | Gly | His | Ile | Gly |     |
|     | 145 |     |     |     |     | 150 |     |     |     |     | 155 |     |     |     |     |     |
| CTA | TTA | ACC | TCA | AGC | CAA | GTG | AAA | GGG | TAT | ATT | AAA | GAA | GGA | CTG | AAC | 743 |
| Leu | Leu | Thr | Ser | Ser | Gln | Val | Lys | Gly | Tyr | Ile | Lys | Glu | Gly | Leu | Asn |     |
| 160 |     |     |     |     | 165 |     |     |     |     | 170 |     |     |     |     |     |     |
| GGC | GGA | GGA | CAA | AAT | ACG | AAT | TAAAAAACGA | AAAAAGACAG | CGGCATATG |   |   |   |   |   |   | 793 |
| Gly | Gly | Gly | Gln | Asn | Thr | Asn |   |   |   |   |   |   |   |   |   |     |
| 175 |     |     |     |     | 180 |     |   |   |   |   |   |   |   |   |   |     |

( 2 ) INFORMATION FOR SEQ ID NO:2:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Val | Ile | Phe | Val | Lys | Lys | Arg | Ser | Leu | Gln | Ile | Leu | Ile | Ala | Leu | Ala |
|---|---|---|---|---|---|---|---|---|---|---|---|---|---|---|---|
| -32 |  | -30 |  |  |  | -25 |  |  |  |  | -20 |  |  |  |  |

| Leu | Val | Ile | Gly | Ser | Met | Ala | Phe | Ile | Gln | Pro | Lys | Glu | Ala | Lys | Ala |
|---|---|---|---|---|---|---|---|---|---|---|---|---|---|---|---|
|  | -15 |  |  |  |  | -10 |  |  |  |  | -5 |  |  |  |  |

| Ala | Glu | His | Asn | Pro | Val | Val | Met | Val | His | Gly | Ile | Gly | Gly | Ala | Ser |
|---|---|---|---|---|---|---|---|---|---|---|---|---|---|---|---|
| 1 |  |  |  | 5 |  |  |  |  | 10 |  |  |  |  | 15 |  |

| Tyr | Asn | Phe | Phe | Ser | Ile | Lys | Ser | Tyr | Leu | Ala | Thr | Gln | Gly | Trp | Asp |
|---|---|---|---|---|---|---|---|---|---|---|---|---|---|---|---|
|  |  |  | 20 |  |  |  |  | 25 |  |  |  |  | 30 |  |  |

| Arg | Asn | Gln | Leu | Tyr | Ala | Ile | Asp | Phe | Ile | Asp | Lys | Thr | Gly | Asn | Asn |
|---|---|---|---|---|---|---|---|---|---|---|---|---|---|---|---|
|  |  | 35 |  |  |  |  | 40 |  |  |  |  | 45 |  |  |  |

| Arg | Asn | Asn | Gly | Pro | Arg | Leu | Ser | Arg | Phe | Val | Lys | Asp | Val | Leu | Asp |
|---|---|---|---|---|---|---|---|---|---|---|---|---|---|---|---|
|  | 50 |  |  |  |  | 55 |  |  |  |  | 60 |  |  |  |  |

| Lys | Thr | Gly | Ala | Lys | Lys | Val | Asp | Ile | Val | Ala | His | Ser | Met | Gly | Gly |
|---|---|---|---|---|---|---|---|---|---|---|---|---|---|---|---|
| 65 |  |  |  |  | 70 |  |  |  |  | 75 |  |  |  |  | 80 |

| Ala | Asn | Thr | Leu | Tyr | Tyr | Ile | Lys | Asn | Leu | Asp | Gly | Gly | Asp | Lys | Ile |
|---|---|---|---|---|---|---|---|---|---|---|---|---|---|---|---|
|  |  |  |  | 85 |  |  |  |  | 90 |  |  |  |  | 95 |  |

```
Glu Asn Val Val Thr Ile Gly Gly Ala Asn Gly Leu Val Ser Ser Arg
            100                     105                 110

Ala Leu Pro Gly Thr Asp Pro Asn Gln Lys Ile Leu Tyr Thr Ser Val
        115                 120                 125

Tyr Ser Ser Ala Asp Leu Ile Val Val Asn Ser Leu Ser Arg Leu Ile
    130                 135                 140

Gly Ala Arg Asn Ile Leu Ile His Gly Val Gly His Ile Gly Leu Leu
145                 150                 155                 160

Thr Ser Ser Gln Val Lys Gly Tyr Ile Lys Glu Gly Leu Asn Gly Gly
                165                 170                 175

Gly Gln Asn Thr Asn
            180
```